US011957632B2

(12) United States Patent
Soreefan et al.

(10) Patent No.: US 11,957,632 B2
(45) Date of Patent: Apr. 16, 2024

(54) WIRELESSLY CHARGED PATIENT SUPPORT APPARATUS SYSTEM

(71) Applicant: Hill-Rom Services, Inc., Batesville, IN (US)

(72) Inventors: Ibne Soreefan, West Chester, OH (US); Douglas A. Seim, Okeana, OH (US); Clementine Pirio, Vannes (FR); Philippe Kaikenger, Pluvigner (FR)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 17/490,688

(22) Filed: Sep. 30, 2021

(65) Prior Publication Data

US 2022/0104979 A1 Apr. 7, 2022

Related U.S. Application Data

(60) Provisional application No. 63/086,666, filed on Oct. 2, 2020.

(51) Int. Cl.
*A61G 7/018* (2006.01)
*A61B 5/11* (2006.01)
(Continued)

(52) U.S. Cl.
CPC ............... *A61G 7/018* (2013.01); *A61B 5/11* (2013.01); *A61G 7/012* (2013.01); *A61G 7/0528* (2016.11);
(Continued)

(58) Field of Classification Search
CPC .... A61G 7/05; A61G 7/0524; A61G 2203/20; A61G 2203/22; A61G 2203/30;
(Continued)

(56) References Cited

U.S. PATENT DOCUMENTS 5,279,011 A 1/1994 Schnelle
5,592,153 A 1/1997 Welling et al.
(Continued)

FOREIGN PATENT DOCUMENTS

DE 102016211178 A1 12/2017
DE 102017011325 A1 6/2018
(Continued)

OTHER PUBLICATIONS

Stryker, Spirit Behavioral Health Platform Bed, Accessed via the Internet at https://www.stryker.com/content/dam/stryker/acute-care/products/spiritselect/resources/Spirit%20Behavioral%20Health%20Platform_SS_Mkt%20Lit-1049.pdf.
(Continued)

*Primary Examiner* — Justin C Mikowski
*Assistant Examiner* — Deborah Talitha Gedeon
(74) *Attorney, Agent, or Firm* — Price Heneveld LLP

(57) ABSTRACT

A charging system for a medical facility includes a patient support apparatus that has a base frame, an upper frame, a wheel to engage a floor surface, and a controller. A rechargeable battery is operably coupled to the base frame. The controller is configured to communicate with the rechargeable battery. A transmitting assembly is coupled to at least one of a wall surface and the floor surface of said medical facility. A receiving assembly is operably coupled to the base frame adjacent to the wheel. The receiving assembly is in communication with the rechargeable battery. The receiving assembly and the transmitting assembly selectively communicate to charge the rechargeable battery. An alert feature is in communication with the controller of the patient support apparatus. The alert feature is configured to emit an alarm when the controller indicates the rechargeable battery is at or below a predetermined charge level.

14 Claims, 25 Drawing Sheets

(51) Int. Cl.
    *A61G 7/012*     (2006.01)
    *A61G 7/05*     (2006.01)
    *A61G 7/057*     (2006.01)
    *A61G 7/10*     (2006.01)
    *A61G 99/00*     (2006.01)
    *G16H 40/67*     (2018.01)
    *H02J 50/40*     (2016.01)
    *H04B 5/00*     (2006.01)

(52) U.S. Cl.
    CPC ........... *A61G 7/05769* (2013.01); *A61G 7/10* (2013.01); *A61G 99/00* (2013.01); *G16H 40/67* (2018.01); *H02J 50/40* (2016.02); *H02J 50/402* (2020.01); *H04B 5/0037* (2013.01)

(58) Field of Classification Search
    CPC .... A61G 7/0528; A61G 7/10; A61G 7/05769; A61G 99/00; A61G 7/018; A61G 7/002; A61G 7/005; A61G 7/008; A61G 7/012; A61G 7/015; A61G 7/0573; A61G 12/005; A61G 12/007; A61B 5/11; A61B 5/6892; H02J 50/402; H02J 50/40; H04B 5/0037; G16H 40/67
    See application file for complete search history.

(56) References Cited

U.S. PATENT DOCUMENTS

| | | |
|---|---|---|
| 5,708,993 A | 1/1998 | Campbell et al. |
| 6,005,486 A | 12/1999 | Fridley et al. |
| 6,781,517 B2 | 8/2004 | Moster et al. |
| 6,902,019 B2 * | 6/2005 | Heimbrock ........... A61G 1/0268 180/19.1 |
| 6,972,543 B1 | 12/2005 | Wells |
| 7,225,488 B2 | 6/2007 | Wu |
| 7,500,280 B2 | 3/2009 | Dixon et al. |
| 7,610,637 B2 | 11/2009 | Menkedick et al. |
| 7,617,555 B2 | 11/2009 | Romano et al. |
| 7,782,046 B2 | 8/2010 | Anderson |
| 7,828,092 B2 | 11/2010 | Vogel et al. |
| 7,887,113 B2 | 2/2011 | Ambarth et al. |
| 7,902,817 B2 | 3/2011 | Anderson |
| 8,026,821 B2 | 9/2011 | Reeder et al. |
| 8,031,080 B2 | 10/2011 | Price et al. |
| 8,143,846 B2 | 3/2012 | Herman et al. |
| 8,240,410 B2 | 8/2012 | Heimbrock et al. |
| 8,341,777 B2 | 1/2013 | Hensley et al. |
| 8,344,860 B2 | 1/2013 | Collins, Jr. et al. |
| 8,410,943 B2 | 4/2013 | Metz et al. |
| 8,477,076 B1 | 7/2013 | Nero, Jr. et al. |
| 8,477,077 B1 | 7/2013 | Nero, Jr. et al. |
| 8,674,839 B2 | 3/2014 | Zerhusen et al. |
| 8,864,205 B2 | 10/2014 | Lemire et al. |
| 9,289,336 B2 | 3/2016 | Lambarth et al. |
| 9,655,457 B2 | 5/2017 | Meyer et al. |
| 9,673,658 B2 * | 6/2017 | Jeong .................... H02J 7/0018 |
| 9,700,247 B2 | 7/2017 | Dixon et al. |
| 10,070,789 B2 | 9/2018 | Collins, Jr. et al. |
| 10,123,925 B2 | 11/2018 | Herman et al. |
| 10,391,008 B2 | 8/2019 | Zerhusen et al. |
| 10,561,551 B2 | 2/2020 | Lambarth et al. |
| 10,583,058 B2 | 3/2020 | Riley et al. |
| 2006/0058587 A1 | 3/2006 | Heimbrock et al. |
| 2011/0247135 A1 | 10/2011 | Herman et al. |
| 2012/0312196 A1 | 12/2012 | Newkirk |
| 2016/0038361 A1 * | 2/2016 | Bhimavarapu ........ A61G 7/018 398/115 |
| 2016/0331614 A1 * | 11/2016 | Furman ................. A61G 7/005 |
| 2018/0333317 A1 | 11/2018 | Zerhusen et al. |
| 2019/0123587 A1 * | 4/2019 | Titov ....................... A61G 7/05 |
| 2019/0123598 A1 * | 4/2019 | Patmore ............... A61G 7/0514 |
| 2019/0229559 A1 * | 7/2019 | Boccoleri ............ A61G 12/008 |
| 2019/0252902 A1 * | 8/2019 | Koch ...................... H02J 50/10 |
| 2019/0265691 A1 | 8/2019 | Agrawal et al. |

FOREIGN PATENT DOCUMENTS

| | | |
|---|---|---|
| EP | 0918502 B1 | 1/2001 |
| EP | 2178483 B1 | 10/2014 |
| EP | 2839819 B1 | 7/2018 |
| EP | 2973460 B1 | 3/2020 |

OTHER PUBLICATIONS

Hillrom, Progressa Bed, Instructions for Use (171528 REV 9); 116 pages.

* cited by examiner

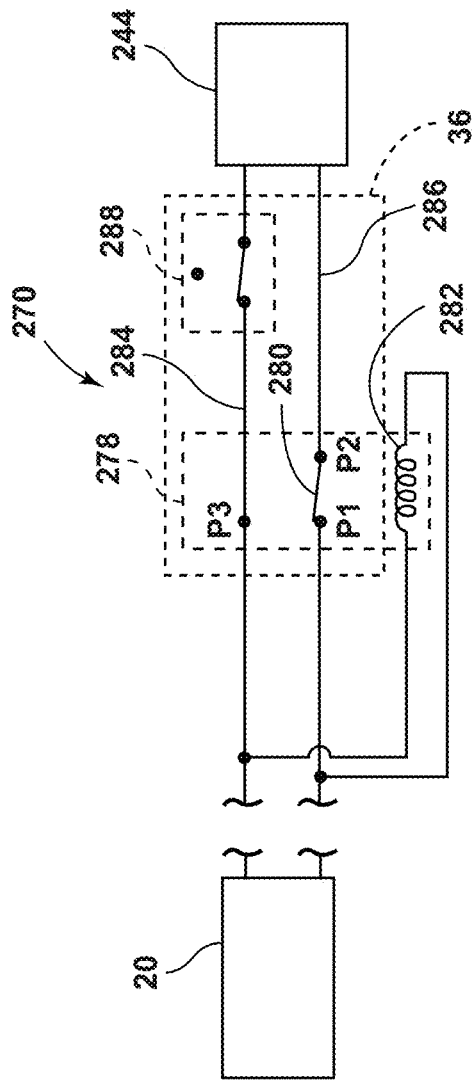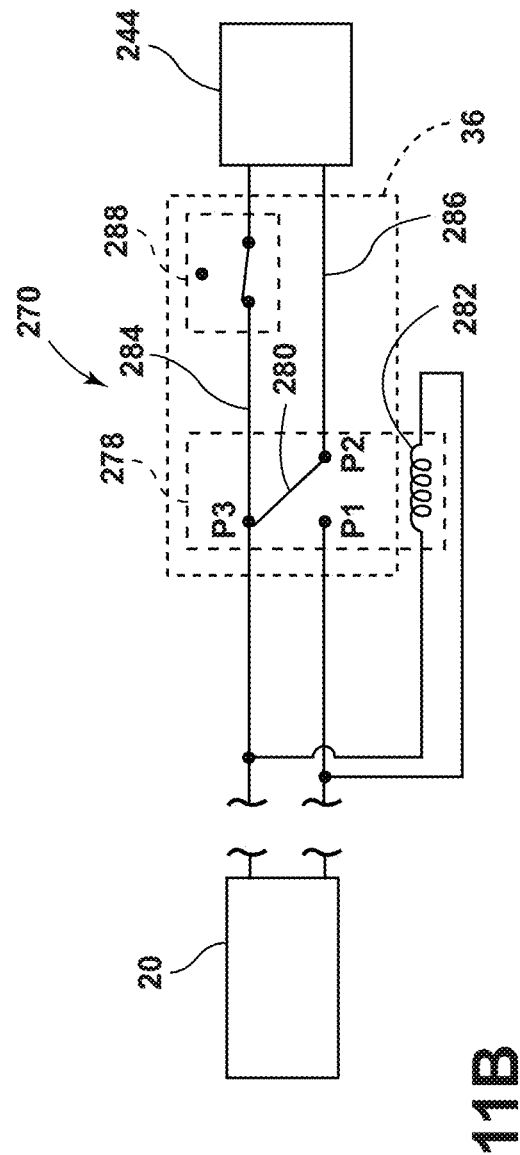

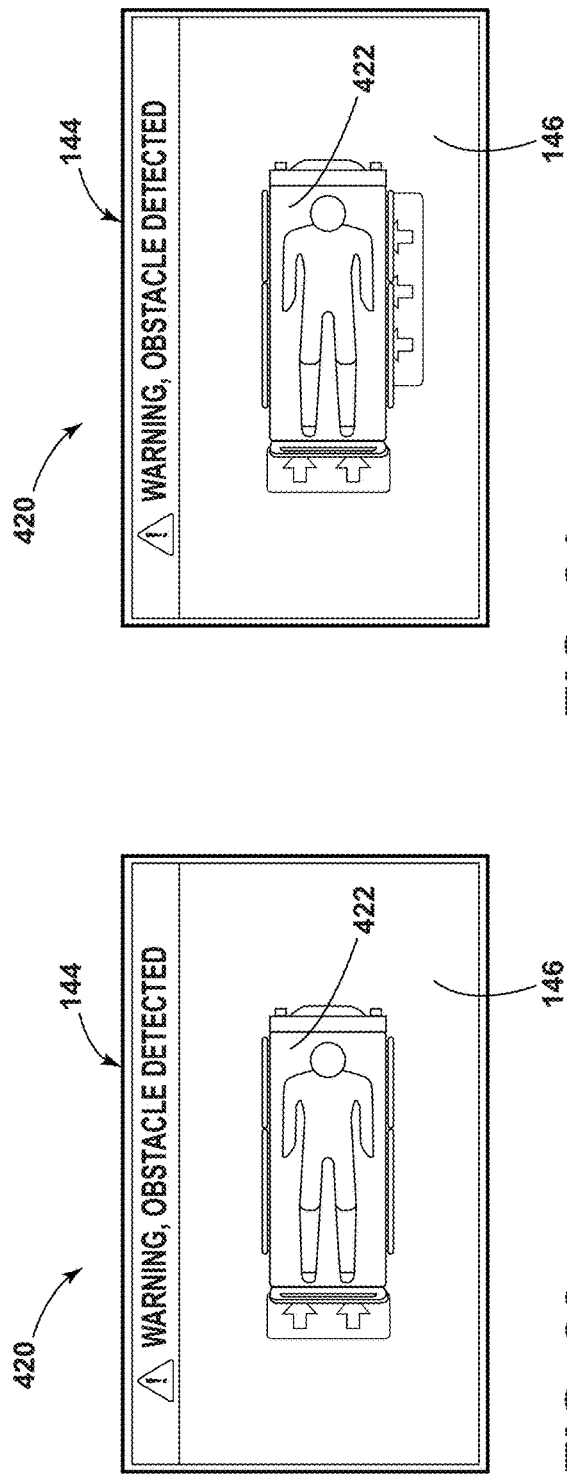

WIRELESSLY CHARGED PATIENT SUPPORT APPARATUS SYSTEM

CROSS-REFERENCE TO RELATED APPLICATION

This application claims priority to and the benefit under 35 U.S.C. §119(e) of U.S. Provisional Application No. 63/086,666, filed on Oct. 2, 2020, entitled "WIRELESSLY CHARGED PATIENT SUPPORT APPARATUS SYSTEM," the disclosure of which is hereby incorporated herein by reference in its entirety.

FIELD OF THE DISCLOSURE

The present disclosure generally relates to a wirelessly charged patient support apparatus system for charging a rechargeable battery on a patient support apparatus.

SUMMARY OF THE DISCLOSURE

According to one aspect of the present disclosure, a charging system for a medical facility includes a patient support apparatus that has a base frame, an upper frame coupled to the base frame, a wheel operably coupled to the base frame to engage a floor surface, and a controller operably coupled to at least one of the base frame and the upper frame. A rechargeable battery is operably coupled to the base frame. The controller is configured to communicate with the rechargeable battery. A transmitting assembly is coupled to at least one of a wall surface and the floor surface of said medical facility. A receiving assembly is operably coupled to the base frame adjacent to the wheel. The receiving assembly is in communication with the rechargeable battery. The receiving assembly and the transmitting assembly selectively communicate to charge the rechargeable battery. An alert feature is in communication with the controller of the patient support apparatus. The alert feature is configured to emit an alarm when the controller indicates the rechargeable battery is at or below a predetermined charge level.

According to another aspect of the present disclosure, an apparatus charging system includes a patient support apparatus including a base frame, wheels coupled to the base frame and configured to engage a floor surface, and a controller. A rechargeable battery is coupled to the patient support apparatus and in communication with the controller. A receiving assembly is coupled to the patient support apparatus. The receiving assembly is coupled to the base frame at a height that is approximately equal to a height of the wheel. The receiving assembly is in communication with the rechargeable battery. A transmitting assembly is configured to selectively communicate with the receiving assembly to charge the rechargeable battery.

According still to another aspect of the present disclosure, a charging system for a medical facility includes a patient support apparatus that has a frame. A wheel is operably coupled to the frame to engage a floor surface. A transmitting assembly has a floor primary element operably coupled to the floor surface and a wall primary element operably coupled to a wall surface in the medical facility. A rechargeable battery is operably coupled to the patient support apparatus. A receiving assembly has a floor secondary element oriented in a first direction to communicate with the floor primary element and a wall secondary element oriented in a second direction to communicate with the wall primary element. The transmitting assembly and the receiving assembly selectively communicate to charge the rechargeable battery.

According to yet another aspect of the present disclosure, a charging system for a patient support apparatus includes a rechargeable battery that supports one or more of the following powered components of the patient support apparatus: an indicator light; an alignment feature; a charge disruption feature; a user interface; an alert feature; an adjustable frame; a lift system; a drive system; a brake system; personal remote devices coupled with the patient support apparatus; external device interfaces of an accessory module; charger ports of an accessory module; a charger port of a pendant; a patient control panel; a patient control panel in communication with at least one of the patient support apparatus, a television, a music device, a telephone, a nurse call system, Internet, a curtain, a room light, and a thermostat; a patient monitoring system including an exit alert light, a pressure sensor, and a photoelectric sensor; a lamp; an obstacle detection system including obstacle sensors; a pneumatic system including a pump; a health monitoring system including a vital signs alert and physiological sensors, such as a force sensor, a pulse oximetry sensor, a heart rate sensor, temperature sensor, and a respiration sensor; a microclimate management system including a blower; a mattress comfort system including a projector; a communication system including a wired/wireless interface and a network interface unit; a mattress associated with wireless communication modules; a procedure monitoring system; and a controller of the patient support apparatus that communicates with external systems or devices including at least one or more of a remote device, a remote server, a nurse call system, and a medical facility network.

These and other features, advantages, and objects of the present disclosure will be further understood and appreciated by those skilled in the art by reference to the following specification, claims, and appended drawings.

BRIEF DESCRIPTION OF THE DRAWINGS

In the drawings:

FIG. 11A is a schematic block diagram of a brake system in a driving mode of operation, according to the present disclosure;

FIG. 11B is a schematic block diagram of the brake system of FIG. 11A in a braking mode;

FIG. 20 is a schematic view of a graphical alert from an obstacle detection system of a patient support apparatus;

FIG. 21 is a schematic view of an additional graphical alert from an obstacle detection system of a patient support apparatus;

FIG. 22 is a schematic view of another graphical alert from an obstacle detection system of a patient support apparatus;

DETAILED DESCRIPTION

Figure 1:
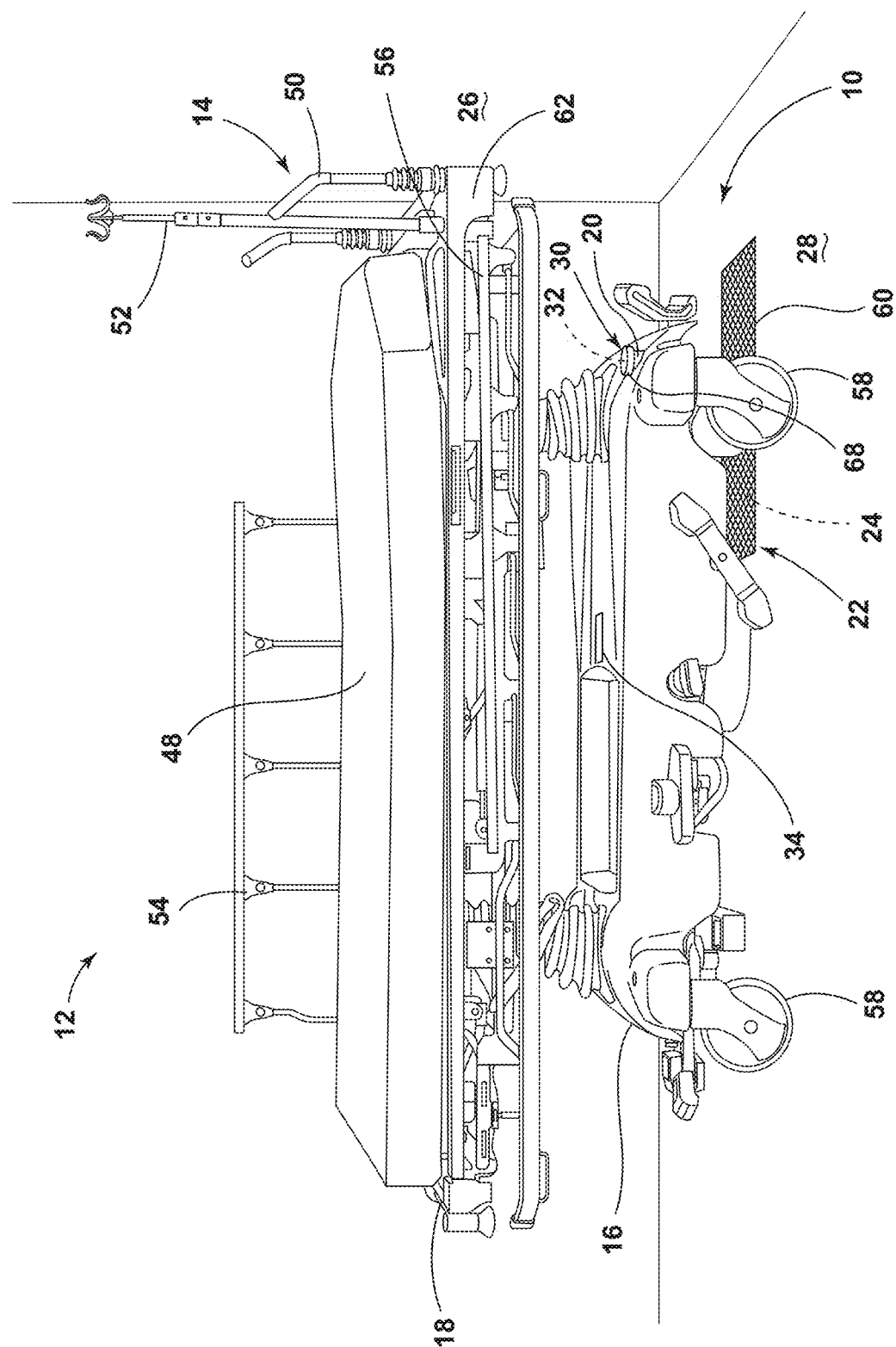
FIG. 1 is a side perspective view of a patient support apparatus disposed over a transmitting assembly of a wireless charging system in a medical facility, according to the present disclosure.

The present illustrated embodiments reside primarily in combinations of method steps and apparatus components related to a wireless charging system. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

For purposes of description herein, the terms "upper," "lower," "right," "left," "rear," "front," "vertical," "horizontal," and derivatives thereof, shall relate to the disclosure as oriented in FIG. 1. Unless stated otherwise, the term "front" shall refer to a surface closest to an intended viewer, and the term "rear" shall refer to a surface furthest from the intended viewer. However, it is to be understood that the disclosure may assume various alternative orientations, except where expressly specified to the contrary. It is also to be understood that the specific structures and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a . . . " does not, without more constraints, preclude the existence of additional identical elements in the process, method, article, or apparatus that comprises the element.

Referring to FIGS. 1-28, reference numeral 10 generally designates a charging system for a medical facility 12. A patient support apparatus 14 has a base frame 16 and an upper frame 18. A rechargeable battery 20 is operably coupled to the base frame 16. A transmitting assembly 22 includes a primary element 24 and is disposed proximate at least one of a wall surface 26 and a floor surface 28. A receiving assembly 30 is operably coupled to the base frame 16 and includes a secondary element 32. The primary element 24 and the secondary element 32 selectively communicate via at least one of capacitive coupling and inductive coupling to charge the rechargeable battery 20. An alert feature 34 is in communication with a controller 36 of the patient support apparatus 14. The alert feature 34 activates an alarm when the controller 36 indicates the rechargeable battery 20 is at or below a predetermined charge level.

Referring to FIG. 1, the patient support apparatus 14 is illustrated as a transport stretcher within the medical facility 12. It is contemplated that the patient support apparatus 14 may be other types of stretchers, medical beds, other types of beds, mattresses, examination tables, operating tables, recliners, or any other suitable structures for supporting a patient without departing from the teachings herein. Moreover, the medical facility 12 may be any suitable location for providing treatment to the patient on the patient support apparatus 14.

The upper frame 18 is coupled to the base frame 16 and is generally adjustable relative to the base frame 16 (e.g., height, tilt, etc.). The upper frame 18 includes a support surface for supporting a mattress 48. The support surface may have adjustable components, such that different portions of the mattress 48 may be adjustable relative to the upper frame 18. For example, a head end or a foot end of the mattress 48 may extend upward at an angle relative to the support surface of the upper frame 18.

The patient support apparatus 14 includes various features for transporting and treating patients. For example, the patient support apparatus 14 includes handles 50 for transporting the patient support apparatus 14 to different locations in the medical facility 12. The patient support apparatus 14 includes an intravenous (IV) pole 52 disposed proximate the handles 50 for supporting medical equipment or medication. The patient support apparatus 14 also includes siderail assemblies 54, 56 extending partially along the length of opposing sides of the upper frame 18. The siderail assemblies 54, 56 are operable between a raised position and a lowered position to transport or access the patient, respectively, as well as prevent or allow ingress and egress. Additional features may be included on or associated with the patient support apparatus 14 without departing from the teachings herein.

Referring still to FIG. 1, the base frame 16 is supported on casters or wheels 58 that engage the underlying floor surface 28 of the medical facility 12. The wheels 58 are generally coupled to the base frame 16 via an axle. The wheels 58 may be configured to rotate in a power drive mode in order to propel the patient support apparatus 14 for transportation by a caregiver, a medical professional, or other users. Each user of the patient support apparatus 14 may be described herein as the caregiver.

Figure 2:
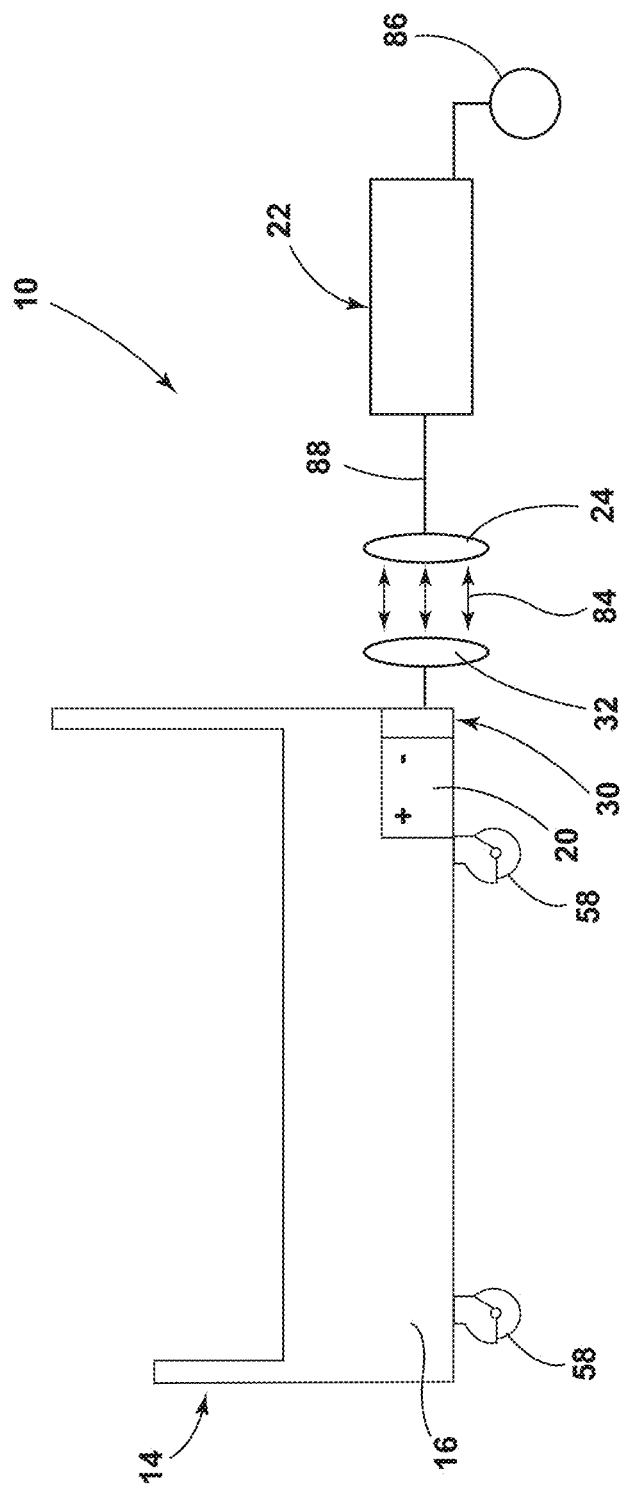
FIG. 2 is a schematic diagram of a wireless charging system for a patient support apparatus, according to the present disclosure.

Referring again to FIG. 1, as well as FIG. 2, the rechargeable battery 20 is generally coupled to the base frame 16 of the patient support apparatus 14 adjacent to one of the wheels 58, as illustrated in the exemplary configuration. However, the rechargeable battery 20 may be operably coupled to the patient support apparatus 14 in any practicable location that provides for wireless charging by the charging system 10. Wireless charging may be advantageous for limiting electrical cords within the medical facility 12, provide more flexibility for charging the patient support apparatus 14 in various locations within the medical facility 12 and minimize the time and effort needed by caregivers to recharge the patient support apparatus 14.

The charging system 10 includes the primary element 24 of the transmitting assembly 22 is in selective communication with the secondary element 32 of the receiving assembly 30 for wirelessly charging the rechargeable battery 20. The transmitting assembly 22 is operably coupled with a surface within the medical facility 12. Generally, multiple transmitting assemblies 22 may be arranged around the medical facility 12, for example, in an emergency department, outpatient bays, patient rooms, hallways, or a combination thereof.

The transmitting assembly 22 may include a mat, a pad, or another housing feature 60 for housing and protecting the primary element 24. As illustrated in FIG. 1, the transmitting assembly 22 is operably coupled to the floor surface 28 of the medical facility 12. The transmitting assembly 22 may be disposed on the floor surface 28, flush with the floor surface 28, disposed below the floor surface 28, or protrude slightly above the floor surface 28. The transmitting assembly 22 may be disposed within the protective housing feature 60 and coupled to the floor surface 28, be coupled directly to the floor surface 28, or be integrally formed with the floor surface 28. Depending on the configuration of the transmitting assembly 22, it is contemplated that the transmitting assembly 22 may be in a fixed location in the medical facility 12, or alternatively may be movable between different locations.

The receiving assembly 30 is operably coupled to the patient support apparatus 14 and communicatively coupled with the rechargeable battery 20. For example, in the illustrated configuration of FIG. 1, the receiving assembly 30 is coupled to the base frame 16 of the patient support apparatus 14 proximate to a head end 62 with the handles 50. The secondary element 32 of the receiving assembly 30 is configured to selectively communicate with the primary element 24 of the transmitting assembly 22. The receiving assembly 30 operates to extract power from the interaction between the primary element 24 and the secondary element 32 and relays the power to the rechargeable battery 20.

Referring still to FIGS. 1 and 2, the patient support apparatus 14 is configured to be moved relative to the transmitting assembly 22 to selectively charge the rechargeable battery 20 or cease charging the rechargeable battery 20. The movement also allows the patient support apparatus 14 to be moved completely away from the transmitting assembly 22, which is advantageous for moving the patient support apparatus 14 with an at least partially charged rechargeable battery 20 about the medical facility 12.

In the illustrated configuration of FIG. 1 with the transmitting assembly 22 operably coupled with the floor surface 28, the patient support apparatus 14 is disposed at least partially over the transmitting assembly 22 to align the primary element 24 with the secondary element 32. The patient support apparatus 14 is rolled or moved until the portion of the base frame 16 with the receiving assembly 30 is positioned over the transmitting assembly 22 on the floor surface 28. The secondary element 32 is generally disposed at a distance in a range up to about 12 inches from the primary element 24 to charge the rechargeable battery 20. This may be a distance between the base frame 16 and the floor surface 28.

The transmitting assembly 22 located on the floor surface 28 may provide greater flexibility for positioning the patient support apparatus 14, and consequently the receiving assembly 30, relative to the transmitting assembly 22. For example, when the transmitting assembly 22 is on the floor surface 28 in a hallway, a side of the patient support apparatus 14 may abut the wall surface 26 so the patient support apparatus 14 does not substantially impede the space in the hallway while allowing the rechargeable battery 20 to charge. In another example, if medical equipment is located proximate to the head end 62 of the patient support apparatus 14 for treating a patient, the patient support apparatus 14 may be spaced from the wall surface 26 and still be disposed over the transmitting assembly 22 on the floor surface 28.

Figure 3:
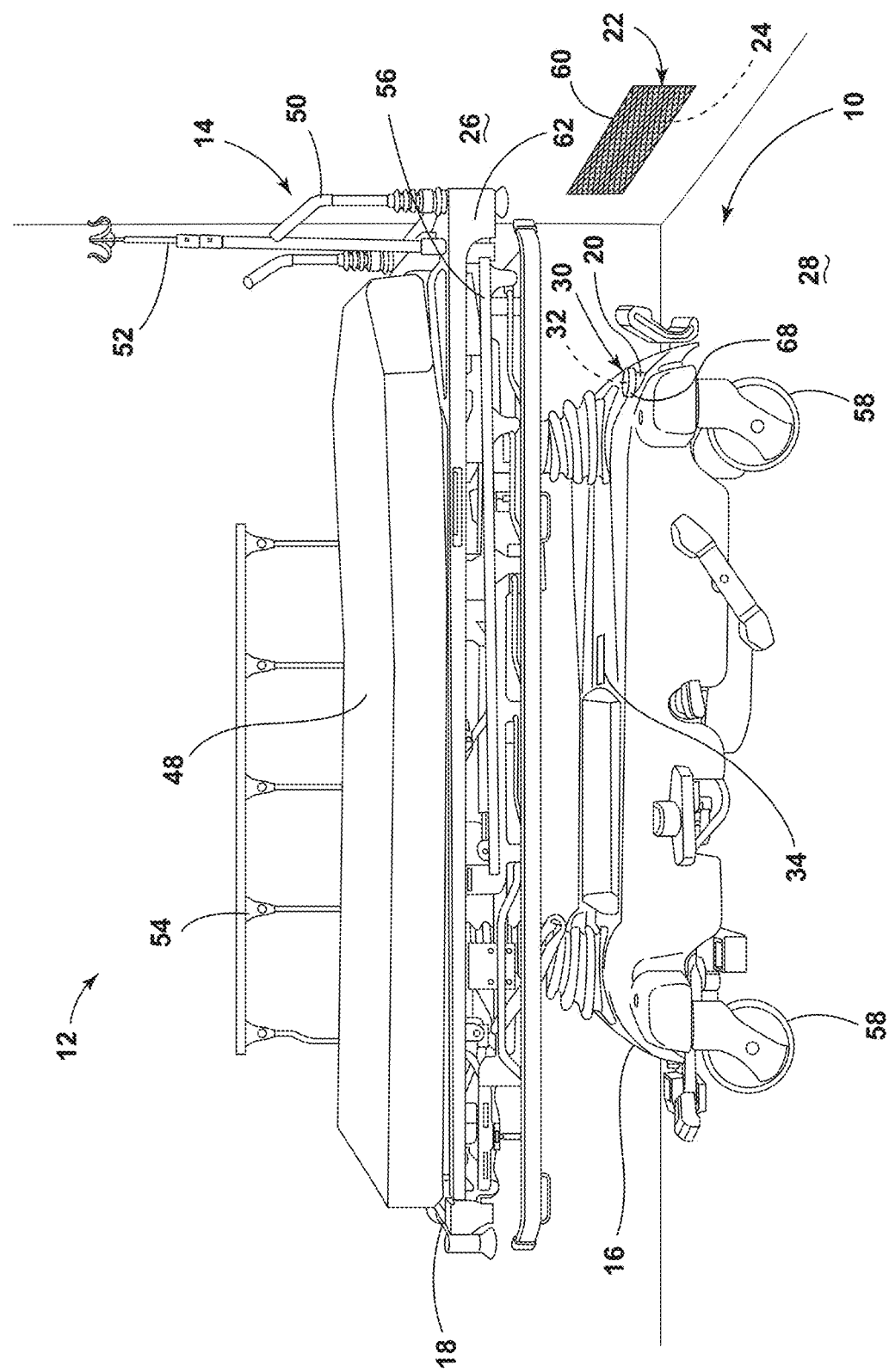
FIG. 3 is a side perspective view of a patient support apparatus disposed adjacent to a transmitting assembly of a wireless charging system in a medical facility, according to the present disclosure.

Referring again to FIG. 2, as well as FIG. 3, the transmitting assembly 22 may be operably coupled with the wall surface 26 of the medical facility 12. The transmitting assembly 22 may be disposed on, flush with, disposed behind, or protrude slightly from the wall surface 26. The transmitting assembly 22 may be disposed within the protective housing feature 60 and coupled to the wall surface 26, be coupled directly to the wall surface 26, or be integrally formed with the wall surface 26. When operably coupled with the wall surface 26, the transmitting assembly 22 is generally disposed proximate the floor surface 28 to align with the secondary element 32 on the patient support apparatus 14.

As the secondary element 32 is generally disposed adjacent to one of the wheels 58, the receiving assembly 30 is disposed at a height that is approximately equal to a height of the wheels 58. In such examples, the primary element 24 is generally disposed at a distance or height from the floor surface 28 that is substantially or approximately equal to a height of the wheels 58 to align with the secondary element 32 for charging. Further, in certain aspects, the rechargeable battery 20 may be disposed adjacent to the receiving assembly 30 at a position substantially equal to the height of the wheels 58. The transmitting assembly 22 on the wall surface 26 may reduce features on the floor surface 28 that can impede the workflow of the caregiver or movement of the patient support apparatus 14 and other medical equipment.

When the receiving assembly 30 is positioned on the base frame 16, the rechargeable battery 20 may be charged when the upper frame 18 of the patient support apparatus 14 is disposed at a variety of heights or angles (e.g., tilts). Additionally, the upper frame 18 may be adjusted with minimal impact on the charging of the rechargeable battery 20. The receiving assembly 30 may include a protective housing feature 68 and the secondary element 32 may be disposed within the housing feature 68. The housing feature 68 may also couple the receiving assembly 30 to the base frame 16 and/or the rechargeable battery 20. Additionally or alternatively, the rechargeable battery 20 may also be disposed within the protective housing feature 68.

To charge the rechargeable battery 20, the patient support apparatus 14 is moved to position the receiving assembly 30 adjacent to the transmitting assembly 22. The secondary element 32 is disposed at a distance in a range up to about 12 inches from the primary element 24. Once aligned, the secondary element 32 and the primary element 24 communicate to recharge the rechargeable battery 20.

Referring again to FIGS. 1-3, in operation, the rechargeable battery 20 is wirelessly charged by the selective interaction between the primary element 24 and the secondary element 32. When the primary element 24 and the secondary element 32 are communicatively coupled, the receiving assembly 30 captures energy from the transmitting assembly 22 to provide power to the rechargeable battery 20. The primary element 24 and the secondary element 32 generally interact through a charging interface 84, which may include at least one of inductive coupling and capacitive coupling.

The primary element 24 is a source configured to transfer power from a power source 86 to the secondary element 32. A wire or cable 88 extends between the primary element 24 and the power source 86. The power source 86 is generally a power supply of the medical facility 12. The transfer of power from the power source 86 to the secondary element 32 may charge (e.g., increase the state of the charge of) the rechargeable battery 20.

In inductive coupling examples, the primary and secondary elements 24, 32 are generally configured as coils. An alternating current is generated through the primary element 24 to create an oscillating magnetic or electromagnetic field between the primary element 24 and the secondary element 32 in the charging interface 84. The electromagnetic field passes through the secondary element 32 to induce an alternating voltage. The receiving assembly 30 includes circuitry 90 to capture or extract power from the electromagnetic field and convert the energy into electricity. The receiving assembly 30 also includes circuitry 90 for directing and controlling the power supplied to the rechargeable battery 20.

In capacitive coupling examples, the primary and secondary elements 24, 32 are generally configured as electrodes. An alternating voltage is applied to the primary element 24 by the power source 86 to generate an oscillating electric field. The electric field generally induces an alternating potential on the secondary element 32. Capacitance is used for the transfer of power between the primary and secondary elements 24, 32, with the space between the primary and secondary elements 24, 32 serving as a dielectric. The receiving assembly 30 includes the circuitry 90 to capture or extract power from the electric field and convert the energy into electricity. The receiving assembly 30 also includes circuitry 90 for directing and controlling the power supplied to the rechargeable battery 20. It is contemplated that other forms of wireless transmission may be employed in the charging system 10, such as, for example, magnetic resonance, loose coupled resonance, and electromagnetic radiation without departing from the teachings herein.

Figure 4:
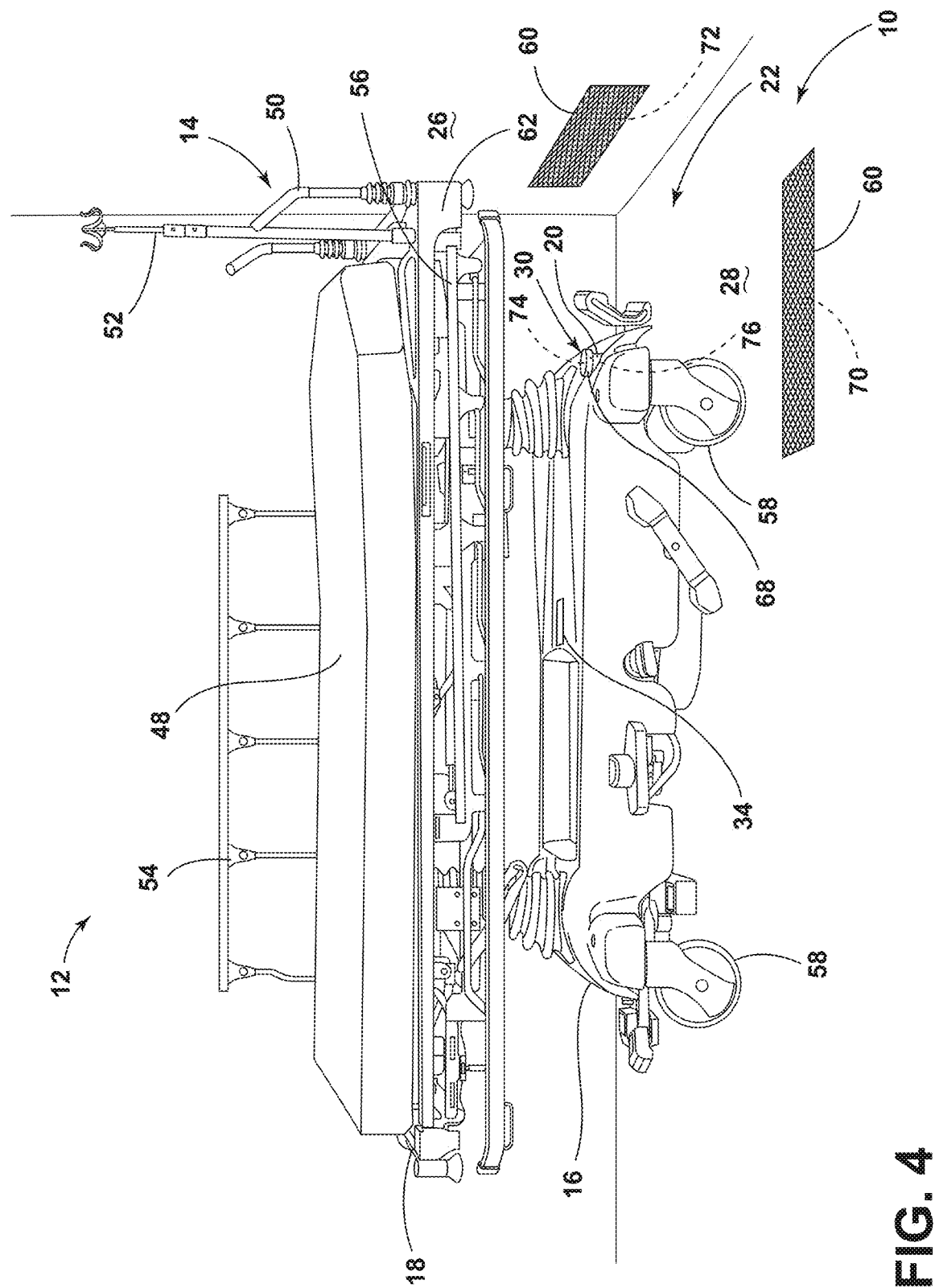
FIG. 4 is a side perspective view of a patient support apparatus disposed adjacent to transmitting assemblies of a wireless charging system in a medical facility, according to the present disclosure.
Figure 5:
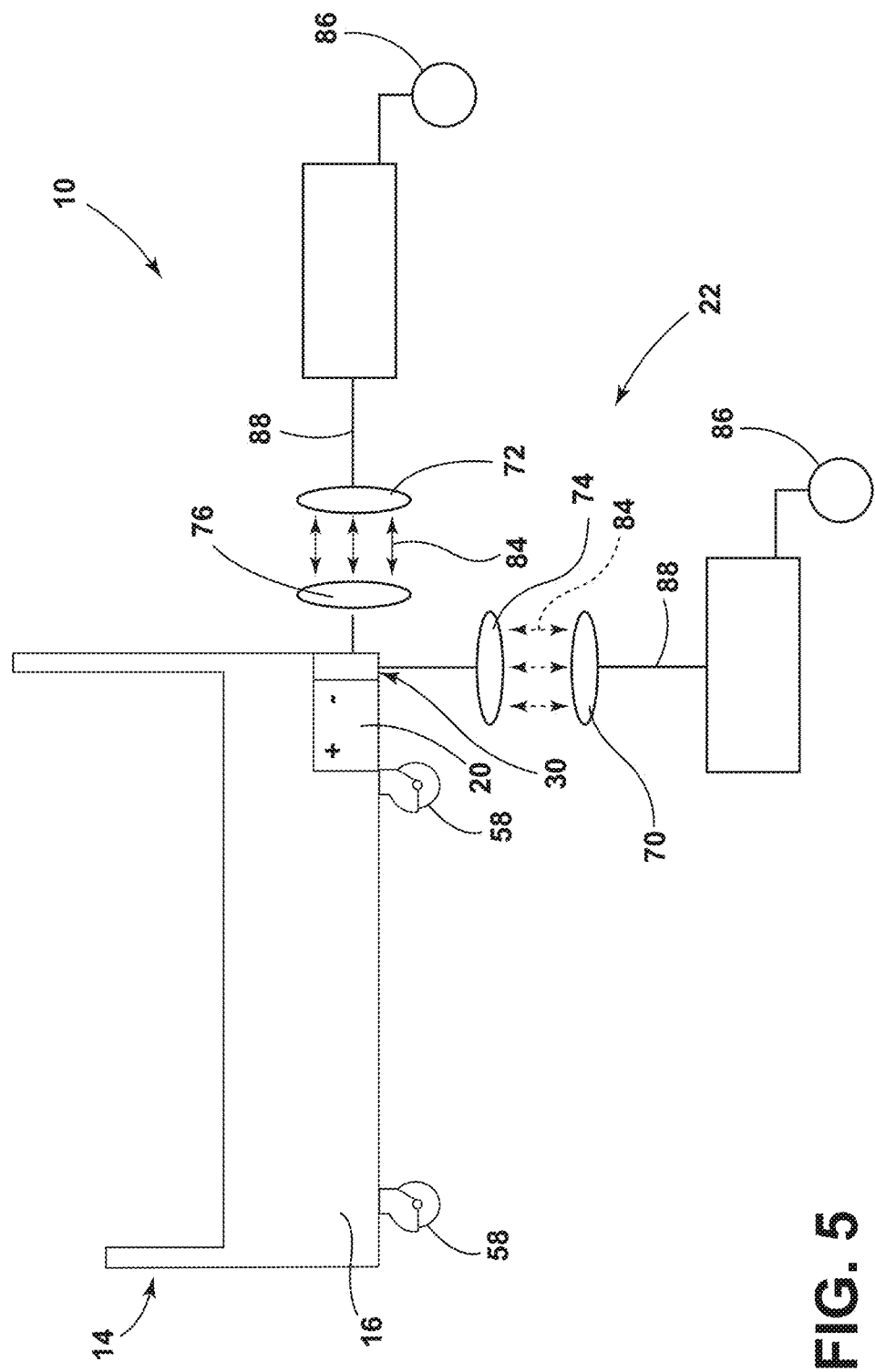
FIG. 5 is a schematic diagram of a wireless charging system for a patient support apparatus, according to the present disclosure.

Referring to FIGS. 4 and 5, the rechargeable battery 20 of the patient support apparatus 14 may be wirelessly charged using the transmitting assembly 22 on the wall surface 26, on the floor surface 28, or a combination thereof. In such configurations, the transmitting assembly 22 includes a floor primary element 70 operably coupled to the floor surface 28 and a wall primary element 72 operably coupled to the wall surface 26. Each of the floor and wall primary elements 70, 72 may be disposed on, flush with, disposed below, or protrude slightly from the surface of the floor or wall, respectively. Additionally or alternatively, each of the floor and wall primary elements 70, 72 may be included in a pad, a mat, or other protective housing 60. The primary elements 70, 72 may be disposed within the protective housing feature 60 coupled to the respective surface 26, 28, coupled directly to the respective surface 26, 28, or integrally formed with the respective surface 26, 28. It is contemplated that each transmitting assembly 22 may include a single floor primary element 70 and a single wall primary element 72, or alternatively, each transmitting assembly 22 may include multiples of one or both of the floor primary element 70 and the wall primary element 72.

The receiving assembly 30 includes a floor secondary element 74 and a wall secondary element 76. The floor secondary element 74 is oriented in a first direction (e.g., downward toward the floor surface 28) to selectively communicate with the floor primary element 70. The wall secondary element 76 is oriented in a second direction, different from the first direction (e.g., toward the wall surface 26) to communicate with the wall primary element 72. Generally, the first direction and the second direction are substantially perpendicular to one another. The floor and wall secondary elements 74, 76, of the receiving assembly 30 may be advantageous for increasing flexibility and convenience of charging the rechargeable battery 20 of the patient support apparatus 14. Accordingly, the rechargeable battery 20 may be charged by one or both of the floor primary element 70 and the wall primary element 72 throughout the medical facility 12 simultaneously or at different times. This may increase efficiency for medical personnel or caregiver who can utilize any configuration of the transmitting assembly 22 that is convenient.

Figure 6:
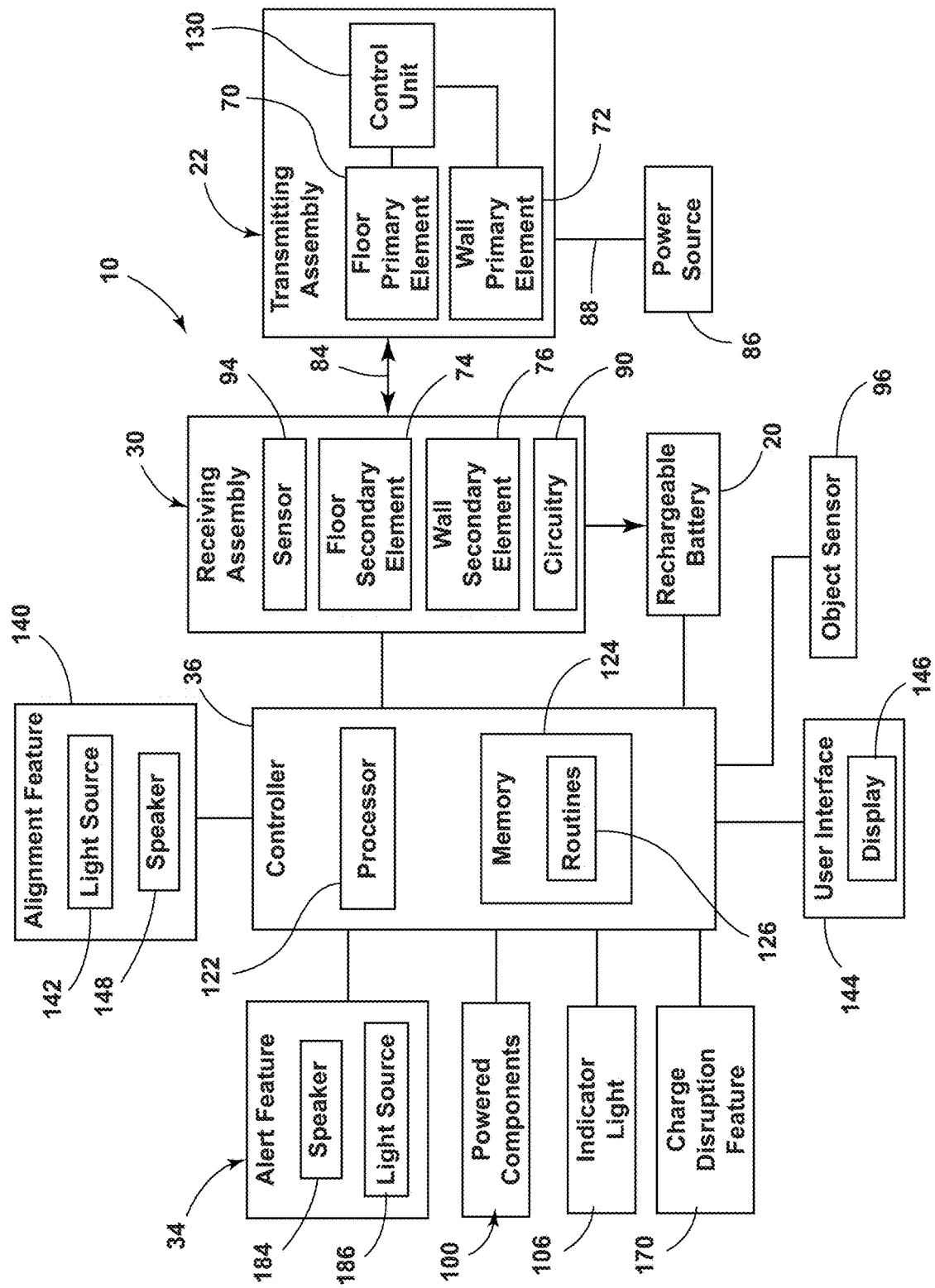
FIG. 6 is a block diagram of a wireless charging system for a patient support apparatus, according to the present disclosure.

Referring to FIG. 6, as well as FIGS. 1-5, a sensor 94 is communicatively coupled with the receiving assembly 30 and senses or detects the transmitting assembly 22. The sensor 94 is configured to sense the electric or electromagnetic field generated by the transmitting assembly 22. The transmitting assembly 22 may intermittently or continuously emit the electric or electromagnetic field until the transmitting assembly 22 is communicatively coupled with the receiving assembly 30. Upon detection of the transmitting assembly 22 by the receiving assembly 30, the charging system 10 may automatically initiate charging the rechargeable battery 20. The receiving assembly 30 captures energy and converts the energy to electricity and supplies the electricity to the rechargeable battery 20.

Additionally or alternatively, the transmitting assembly 22 may include the sensor 94 to detect the receiving assembly 30 or the patient support apparatus 14 and emits the electric or electromagnetic field upon detection of the receiving assembly 30. In such examples, the sensor 94 may sense a signal from the receiving assembly 30, the proximity of the support apparatus 14, etc. Upon sensing the receiving assembly 30 or an object, the transmitting assembly 22 may emit the electric or electromagnetic field. The transmitting assembly 22 may cease emitting the electric or electromagnetic field if the transmitting assembly 22 does not communicate with the receiving assembly 30 within a predefined period of time. Alternatively, the transmitting assembly 22 may continuously emit the electric or electromagnetic field. The electric or electromagnetic field may be constant or increase when communicating with the receiving assembly 30.

Referring still to FIGS. 1-6, the charging system 10 may include an object sensor 96 configured to detect foreign objects that may be disposed between the transmitting assembly 22 and the receiving assembly 30. The foreign objects may impede or prevent the communication between the transmitting assembly 22 and the receiving assembly 30. The support apparatus 14 and/or the charging system 10 may alert the caregiver of sensed foreign objects to allow the caregiver to remove the objects and the rechargeable battery 20 to charge. Such information is advantageous for alerting the caregiver when the rechargeable battery 20 should be charging based on alignment between the transmitting assembly 22 and the receiving assembly 30 but is not. The object sensor 96 may be a proximity sensor, a capacitive sensor, or other sensors for detecting objects. The object sensor 96 may be coupled to the support apparatus 14 proximate to the receiving assembly 30, to the transmitting assembly 22, to the surrounding surface 26, 28 proximate to the transmitting assembly 22, or other practicable locations for detecting objects interfering with the wireless charging.

The transmitting assembly 22 selectively communicates with the receiving assembly 30 to provide power that can be stored in the rechargeable battery 20. The rechargeable battery 20 is utilized to provide various powered components 100 within or operably coupled with the patient support apparatus 14. The powered components 100 generally relate to various functions of the patient support apparatus 14, entertainment for the patient, and treatment or care for the patient. Further, the powered components 100 may include various aspects related to the rechargeable battery 20, including the alert feature 34 that indicates a low charge level, as well as an indicator light 106 indicating a current charging state. Additional examples of the powered components 100 are discussed further herein.

Referring still to FIG. 6, the charging system 10 includes the controller 36 that has a processor 122, a memory 124, and other control circuitry. Instructions or routines 126 are stored within the memory 124 and executable by the processor 122. The controller 36 is communicatively coupled with the rechargeable battery 20 and the receiving assembly 30. The controller 36 monitors the stored electricity in the rechargeable battery 20 and controls the power being provided by the receiving assembly 30. Accordingly, the controller 36 monitors the charge level of the rechargeable battery 20. Additionally or alternatively, the controller 36 may control the receiving assembly 30 to start or stop collecting power and transferring power to the rechargeable battery 20 when the rechargeable battery 20 is at a fully charged level.

It is contemplated that a control unit 130 in the transmitting assembly 22 may control the emission of the electric or electromagnetic field based on the charge level of the rechargeable battery 20. In such configurations, the charge level of the rechargeable battery 20 may be monitored by the controller 36 and communicated to the transmitting assembly 22. Additionally or alternatively, the transmitting assembly 22 may stop generating an electric or electromagnetic field after a predetermined period of time.

The rechargeable battery 20 is configured to hold and store electricity to power the powered components 100 and other features on the patient support apparatus 14. The rechargeable battery 20 is generally a high capacity battery, which holds a charge (e.g., provides power) for a predetermined period of time. The predetermined period of time may be at least 12 hours, which aligns with a full shift for many emergency department personnel. Additionally or alternatively, the rechargeable battery 20 may hold the charge for up to 24 hours, up to 48 hours, up to a week, etc. The amount of charge the rechargeable battery 20 holds may depend on the size of the rechargeable battery 20. Different medical facilities 12 may utilize rechargeable batteries 20 having different capacities. Generally, the rechargeable battery 20 takes approximately four to five hours to fully charge from an empty charge level. However, the rechargeable battery 20 may be partially charged throughout the day as the patient support apparatus 14 moves throughout the medical facility 12 to maintain a full or a substantially full charge level.

With further reference to FIG. 6, the rechargeable battery 20 charges when the receiving assembly 30 is properly positioned relative to the transmitting assembly 22 to capture energy. Proper positioning generally includes the receiving assembly 30 being sufficiently close to the transmitting assembly 22 and properly aligned with the transmitting assembly 22 to provide or generate the charging interface 84. An alignment feature 140 of the charging system 10 may confirm that the receiving assembly 30 is properly positioned relative to the transmitting assembly 22. The alignment feature 140 may also indicate if the receiving assembly 30 is disposed close to the proper position, but is currently misaligned or if no receiving assembly 30 is detected. The alignment feature 140 may provide a visual, audible, or tactile alert that confirms proper alignment and positioning of the receiving assembly 30 relative to the transmitting assembly 22.

In various examples, the alignment feature 140 may provide a visual alert indicative of proper positioning. For example, the alignment feature 140 may include a light source 142 configured to emit light in a certain pattern, color, intensity, etc. when the receiving assembly 30 is properly positioned. In such examples, the light source 142 may emit a first color when the receiving assembly 30 is not detected and a second color when the receiving assembly 30 is properly aligned. Alternatively, the light source 142 may emit a first color when the receiving assembly 30 is not detected, a second color when the receiving assembly 30 is detected but not properly aligned, and a third color when the receiving assembly 30 is properly aligned. Alternatively still, the light source 142 may utilize different intensities of light, patterns of light, flashing of light, etc. to indicate various relationships between the transmitting assembly 22 and the receiving assembly 30.

In another example, the alignment feature 140 may be in communication with a user interface 144. The alignment feature 140 may provide a message on a display 146 of the user interface 144 confirming the receiving assembly 30 is properly positioned or indicating the receiving assembly 30 is misaligned. The user interface 144 may be, for example, coupled with the patient support apparatus 14 (e.g., on a siderail assembly 54, 56), a facility device (e.g., a nurse station status board, nurse call system device, etc.), a device belonging to the caregiver (e.g., a phone), or a combination thereof. In an additional example, the alignment feature 140 may include markers or indicia on the wall surface 26 or the floor surface 28 proximate the transmitting assembly 22. When the receiving assembly 30 or the patient support apparatus 14 are aligned with the markers or indicia, the receiving assembly 30 is in the proper position.

Additionally or alternatively, the alignment feature 140 may provide an audible alert that confirms proper positioning. The alignment feature 140 may include or be in communication with a speaker 148. The speaker 148 may emit a sound when the receiving assembly 30 is properly positioned relative to the transmitting assembly 22. In further non-limiting examples, the alignment feature 140 may provide a tactile or haptic alert. For example, one or both of the handles 50 of the patient support apparatus 14 may move, shake, or jolt when the receiving assembly 30 is in the proper position to charge the rechargeable battery 20.

With reference still to FIG. 6, the alignment feature 140 indicates to the caregiver that the receiving assembly 30 is in a position relative to the transmitting assembly 22 to charge the rechargeable battery 20. The alignment feature 140 may be coupled to the support apparatus 14, to the receiving assembly 30, the transmitting assembly 22, the wall surface 26, the floor surface 28, the user interface 144, any other practicable location that would alert the caregiver of the alignment, or a combination thereof. The charging system 10 may include more than one alignment feature 140 and some or all of the alignment features may be activated simultaneously.

It is contemplated that the alignment feature 140 may be in communication with the sensor 94 to determine whether the receiving assembly 30 is properly positioned or misaligned. In such examples, the alignment feature 140 may indicate when the sensor 94 detects the electric or electromagnetic field of the transmitting assembly 22 and the receiving assembly 30 is properly positioned, slightly misaligned, or substantially misaligned. The sensor 94 may communicate detected information about the electric or electromagnetic field to the controller 36.

The detected information may include, for example, strength or location of the electric or electromagnetic field, direction of a stronger electric or electromagnetic field, etc. For example, the sensor 94 may detect that the electric or electromagnetic field is stronger in an area adjacent to the receiving assembly 30. The controller 36 may indicate to the alignment feature 140 that a stronger electric or electromagnetic field is in the adjacent area and the alignment feature 140 may communicate this information to the caregiver. In a non-limiting example, the user interface 144 may display an arrow indicating where the stronger electric or electromagnetic field is detected. Accordingly, the caregiver can adjust the patient support apparatus 14 based on the detected information to properly align the receiving assembly 30 with the transmitting assembly 22, which may be confirmed by the alignment feature 140.

Referring still to FIG. 6, when the rechargeable battery 20 is in a currently charging state, the controller 36 is configured to activate the indicator light 106. The controller 36 includes one or more routines 126 for identifying that the rechargeable battery 20 is in a currently charging state and subsequently activating the indicator light 106. When activated, the indicator light 106 notifies the caregiver that the rechargeable battery 20 is currently charging. The indicator light 106 may illuminate in different colors, intensities, or patterns based on the current charge level of the rechargeable battery 20. When the rechargeable battery 20 is fully charged or there is a misalignment between the transmitting and receiving assemblies 22, 30, the rechargeable battery 20 may not be in the currently charging state. When the rechargeable battery 20 is not in the currently charging state, the indicator light 106 may be deactivated.

Additionally or alternatively, the indicator light 106 may illuminate at a certain intensity, in a certain color, in a certain pattern, etc. to indicate to the caregiver that the rechargeable battery 20 is at a fully charged level. The indicator light 106 may be included as part of the patient support apparatus 14, the rechargeable battery 20, the receiving assembly 30, the transmitting assembly 22, other features of the charging system 10, or a combination thereof. It is contemplated that the alignment feature 140 may operate before or simultaneously with the indicator light 106. It is also contemplated that the alert feature 34 may also indicate that the rechargeable battery 20 is at the fully charged level without departing from the teachings herein.

As previously stated, the controller 36 monitors the charge level of the rechargeable battery 20. The controller 36 may indicate an estimated time until the rechargeable battery 20 is at a fully charged level. The controller 36 may communicate with the user interface 144 to display the time remaining until the rechargeable battery 20 is at the fully charged level or an estimated time when the rechargeable battery 20 is at the fully charged state. The information may be conveyed to the caregiver through an icon, a numerical value, a graphic, text, etc. on the display 146 of the user interface 144. It is also contemplated that alert feature 34 may convey the information relating to the amount of time until the rechargeable battery 20 without departing from the teachings herein.

Referring still to FIG. 6, the charging system 10 may additionally or alternatively include a charge disruption feature 170 for indicating to the caregiver or medical professional that charging of the rechargeable battery 20 has been disrupted. The charge disruption feature 170 may be part of the alignment feature 140 or alternatively may be a separate feature. The charge disruption feature 170 provides a visual, audible, or tactile alarm when the receiving assembly 30 is no longer in communication with the transmitting assembly 22, and consequently the rechargeable battery 20 is no longer charging. Accordingly, the charge disruption feature 170 activates an alarm when the controller 36 indicates that charging of the rechargeable battery 20 has been disrupted. The charge disruption feature 170 is advantageous for alerting the caregiver that movement of the patient support apparatus 14, whether intentional or inadvertent, stopped the charging of the rechargeable battery 20.

The charge disruption feature 170 may be any visual, audible, or tactile alarm or alert as discussed herein. The charge disruption feature 170 may provide an alert each time the receiving assembly 30 is disengaged from the transmitting assembly 22 or alternatively the charge disruption feature 170 may provide an alert when the charging is disrupted and the rechargeable battery 20 is not in a fully charged level or above a predetermined charge level. For example, as previously stated, the controller 36 monitors the charge level of the rechargeable battery 20 and may also monitor when the receiving assembly 30 is in communication with the transmitting assembly 22. When the receiving assembly 30 is disengaged from the transmitting assembly 22 and the rechargeable battery 20 is at a charge level less than a fully charged level or a predetermined charge level, the charge disruption feature 170 activates an alarm to alert the medical professional of the disengagement when the controller 36 indicates that charging has been disrupted. The predetermined charge level may be a set percentage or may be adjustable by the caregiver. Further, the predetermined charge level may differ based on the medical facility 12 or unit of the medical facility 12 based on typical movement patterns of the patient support apparatus 14.

Figure 7:
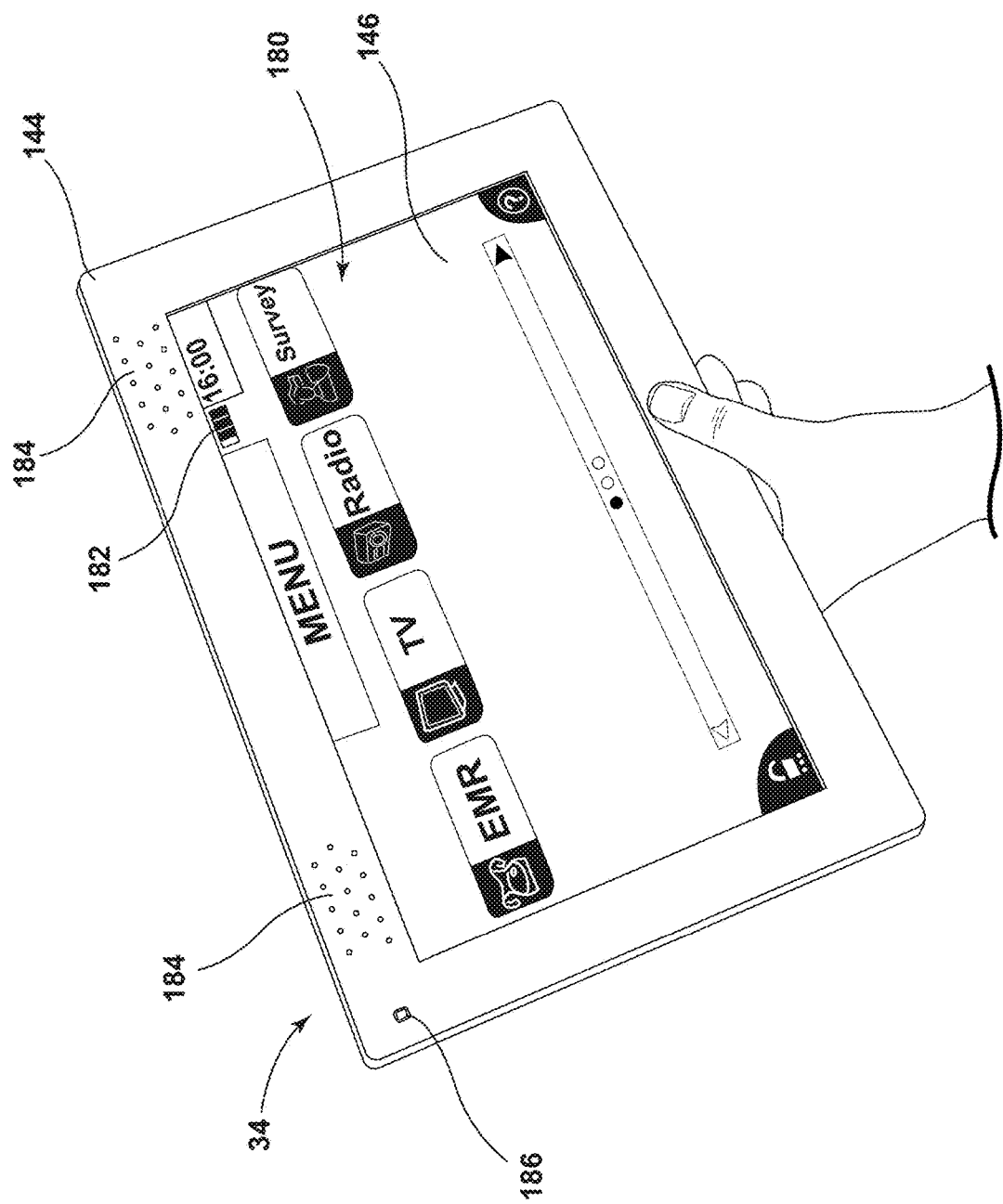
FIG. 7 is a front perspective view of a user interface of a wireless charging system, according to the present disclosure.

Referring again to FIG. 6, as well as FIG. 7, the user interface 144 is in communication with the patient support apparatus 14 through a wired connection or a wireless connection as described further herein. The user interface 144 may be integrated into the patient support apparatus 14 or may be a remote device and communicatively coupled to the patient support apparatus 14. The user interface 144 may be utilized primarily by the patient or the caregiver. The user interface 144 includes the display 146, which may be a touchscreen, with various icons 180 selectable by the patient or the caregiver. In the illustrated configuration in FIG. 7, the selectable icons 180 relate to medical information (e.g., electronic medical records (EMR)), as well as entertainment. The display 146 generally includes a battery charge icon 182, which is indicative of a current charge level of the rechargeable battery 20. The battery charge icon 182 may be a graphic display or alternatively may be a numerical value.

The charging system 10 includes the alert feature 34 for notifying the caregiver within the medical facility 12 when the controller 36 indicates that the rechargeable battery 20 is at or below the predetermined charge level (e.g., a low charge level). The alert feature 34 may be included in the patient support apparatus 14, the rechargeable battery 20, the user interface 144, other features of the charging system 10, or a combination thereof. The alert feature 34 emits an alarm to notify the caregiver of the low charge level. The alarm may be any signal that attracts the attention of the caregiver, which may be an audible, a visible, or a tactile alarm. It is contemplated that the alarm may be changed or programmed by the caregiver. The ability to adjust the alarm may be advantageous to overcome or minimize alarm fatigue that can be felt by the caregiver from hearing or seeing other alarms throughout the medical facility 12.

When the rechargeable battery 20 reaches the low charge level, the rechargeable battery 20 may begin to operate in a low power mode that conserves energy. The alert feature 34 may indicate when the rechargeable battery 20 is in the low power mode. For example, a notification may be displayed on the user interface 144 when the rechargeable battery 20 begins operating in the low power mode. The notification may remain on the display 146 of the user interface 144 until the rechargeable battery 20 exits the low power mode. The rechargeable battery 20 may exit the lower power mode when the rechargeable battery reaches a fully charged level or another predetermined charge level. In another non-limiting example, the indicator light 106 may indicate the low power mode.

As best illustrated in FIG. 7, the alert feature 34 may at least partially be integrated into the user interface 144. In such configurations, the alert feature 34 includes a speaker 184, which is configured to emit an audible alarm indicating the current charge level of the rechargeable battery 20 is at or below the predetermined charge level. Additionally or alternatively, the alert feature 34 includes a light source 186 configured to emit light as a visual alarm that the current charge level is at or below the predetermined charge level. Moreover, the display 146 of the user interface 144 may be used to display a visual alarm using text, a graphic, a design, or combinations thereof.

The alarm may be one or both of the audible and visual alarms and may be different based on different battery charge levels. For example, at or below a first predetermined charge level, the light source 186 may emit light at a first intensity or of a first color. When the rechargeable battery 20 is at or below a second predetermined charge level, which may be less than the first predetermined charge level, the light source 186 may emit light at a second intensity or of a second color. Additionally or alternatively, the user interface 144 may display a first message on the display 146 when the rechargeable battery 20 is at a first predetermined charge level and a second message on the display 146 when the rechargeable battery 20 is at a second predetermined charge level. In an audible alarm example, the user interface 144 may emit a first sound or a sound at a first intensity when the rechargeable battery 20 is at a first predetermined charge level, and emit a second sound or a sound at a second intensity at a second predetermined charge level. It is contemplated that the alert feature 34 may utilize any one or more of the visual, tactile, or audible alerts or alarms as discussed herein.

Referring to FIGS. 1-7, the receiving assembly 30 is generally positioned at one end of the patient support apparatus 14 on the base frame 16 adjacent to one of the wheels 58. In this position, the receiving assembly 30 can selectively communicate with the transmitting assembly 22 operably coupled to the floor surface 28, the transmitting assembly 22 operably coupled to the wall surface 26, or a combination thereof. The receiving assembly 30 is generally positioned to be positioned between about 5 inches to about 12 inches from the transmitting assembly 22 to capture energy emitted from the transmitting assembly 22 and wirelessly charge the rechargeable battery 20.

The charging system 10 may include multiple receiving assemblies 30, each coupled to a respective patient support apparatus 14, and multiple transmitting assemblies 22 disposed around the medical facility 12. Each receiving assembly 30 is configured to selectively communicate with each transmitting assembly 22 when the receiving assembly 30 is moved within the predetermined distance range from the transmitting assembly 22 (e.g., in a range from about 5 inches to about 12 inches). The transmitting assemblies 22 may be arranged in any practicable location in the medical facility 12 including, outpatient bays, patient rooms, hallways, the emergency department, surgical suites, or other practicable locations.

In certain medical settings, such as patient rooms, the patient support apparatus 14 may be disposed in a single location for several hours or days at a time. The receiving assembly 30 may be arranged over the transmitting assembly 22 to continually charge the rechargeable battery 20, and consequently, power the patient support apparatus 14. In other medical settings, such as emergency departments, the patient support apparatus 14 may be moved to different locations of the medical facility 12 every few hours. Generally, in emergency departments, the patient support apparatus 14 is used to retrieve a patient, moved to a location to provide treatment, and then moved to retrieve the next patient.

Depending on the number of patients, an emergency department can have approximately 12 patients per patient support apparatus 14 per day. As such, each patient support apparatus 14 may be utilized for a new patient every one to two hours. Accordingly, the rechargeable battery 20 on each patient support apparatus 14 may be partially charged throughout the day in various locations around the medical facility 12 to maintain power in the patient support apparatus 14. The caregiver can monitor the charge level of the rechargeable battery 20 through the charging system 10 (e.g., the alert feature 34, the user interface 144, etc.). Due to the quick overturn of patients, the wireless charging by the charging system 10 provides convenient and efficient charging of the rechargeable battery 20 without plugging and unplugging the patient support apparatus 14 into the power source 86. This configuration provides more efficient workflow in various medical settings and can reduce clutter in certain spaces around the medical facility 12.

It is contemplated that the charging system 10 may be configured as a separate system, selectively removable from the medical facility 12, the patient support apparatus 14, or a combination thereof. For example, the transmitting assembly 22 may be moved to different locations within the medical facility 12. The transmitting assembly 22 may be moved from the floor surface 28 in one location to the wall surface 26 in a second location. It is also contemplated that the transmitting assembly 22 may be coupled to a separate structure, such as a storage feature, that can be moved to different locations in the medical facility 12.

The receiving assembly 30 may also be selectively coupled to and removed from the patient support apparatus 14. In such examples, the receiving assembly 30 may be used on multiple patient support apparatuses 14 at different times. This configuration may be advantageous for charging some patient support apparatuses 14 while others are sufficiently charged.

Referring still to FIGS. 1-7, the patient support apparatus 14 may include one or more of a variety of powered components 100, which are powered by the rechargeable battery 20 and explained in more detail below. As previously discussed, the rechargeable battery 20 powers various aspects of the charging system 10, such as the indicator light 106, the alignment feature 140, the sensor 94, the charge disruption feature 170, etc. The rechargeable battery 20 may also power the user interface 144 or the alert feature 34 when operably coupled with the patient support apparatus 14.

Figure 8:
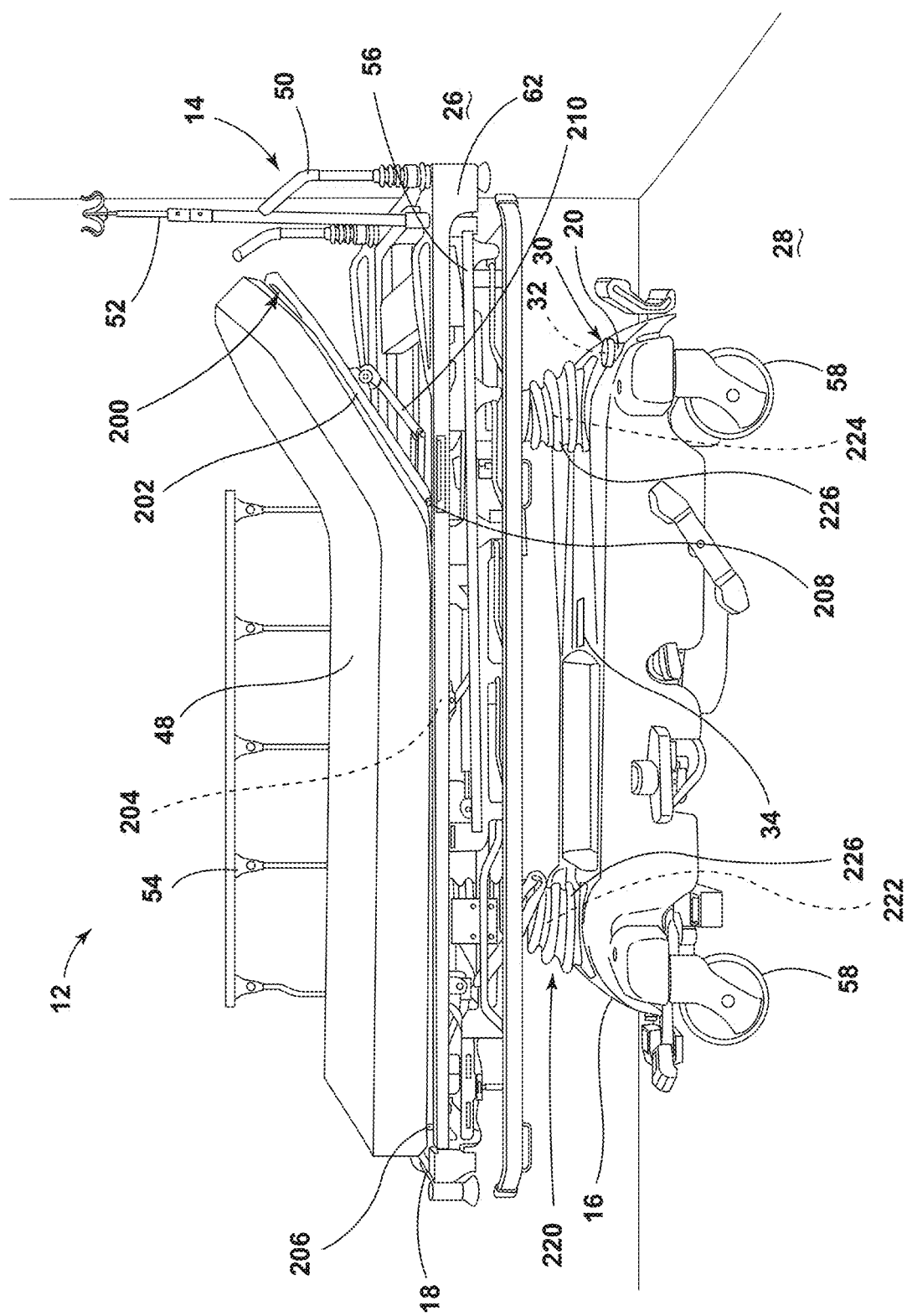
FIG. 8 is a side perspective view of a patient support apparatus with a head end of a mattress in an elevated position, according to the present disclosure.

As illustrated in FIG. 8, the powered component 100 powered by the rechargeable battery 20 may be an adjustable frame 200 utilized for bed articulation, such as to adjust the position of the mattress 48. The mattress 48 may be disposed on the adjustable frame 200 that includes various segments. For example, the adjustable frame 200 may include a head end segment 202, a base or torso segment 204, and a foot end segment 206, each independently adjustable to various angles relative to the remaining segments. Accordingly, the adjustable frame 200 is configured to articulate between various positions. The adjustable frame 200 is positioned on the upper frame 18 of the patient support apparatus 14 and is configured to adjust relative to a base or rest position on the upper frame 18.

In the illustrated example of FIG. 8, the head end segment 202 of the adjustable frame 200 is rotatable about a pivot 208 to extend at an upward angle from the torso segment 204 and the upper frame 18. The head end segment 202 is coupled to an actuator 210. The actuator 210 extends between the adjustable frame 200 and the upper frame 18 and is operably coupled to the rechargeable battery 20. The actuator 210 is configured to raise and lower the head end segment 202 of the adjustable frame 200. The head end segment 202 is generally raised or lowered by extension or retraction of a cylinder of the actuator 210. It is contemplated that the foot end segment 206 may also be coupled to an additional actuator 210 to raise and lower the foot end segment 206 in a similar manner. The mattress 48 may be adjusted between a variety of positions for the treatment or comfort of the patient. It is contemplated that the actuator 210 may be any type of mechanical, electromechanical, hydraulic, or pneumatic device to move the adjustable frame 200.

Referring still to FIG. 8, the rechargeable battery 20 may power a lift system 220 for raising, lowering, and tilting the upper frame 18 relative to the base frame 16. As illustrated in the example of FIG. 8, the lift system 220 includes two actuators 222, 224. The actuator 222 is disposed adjacent to a foot end of the upper frame 18 and controls the vertical position of the foot end. The actuator 224 is disposed adjacent to the head end 62 of the upper frame 18 of the patient support apparatus 14 and controls the vertical position of the head end 62.

Each of the actuators 222, 224 is covered by a flexible cover 226. It is contemplated that the lift system 220 may include any type of mechanical, electromechanical, hydraulic, or pneumatic device to adjust the upper frame 18. An interface may be provided on the patient support apparatus 14 with bed controls for receiving user input commands relating to the bed articulation (e.g., via the adjustable frame 200 or the lift system 220). The interface may be part of the user interface 144 when the user interface 144 is coupled to the patient support apparatus 14 or may be a separate interface for receiving user input commands. It is generally contemplated that the rechargeable battery 20 may provide power to the interface.

Figure 9:
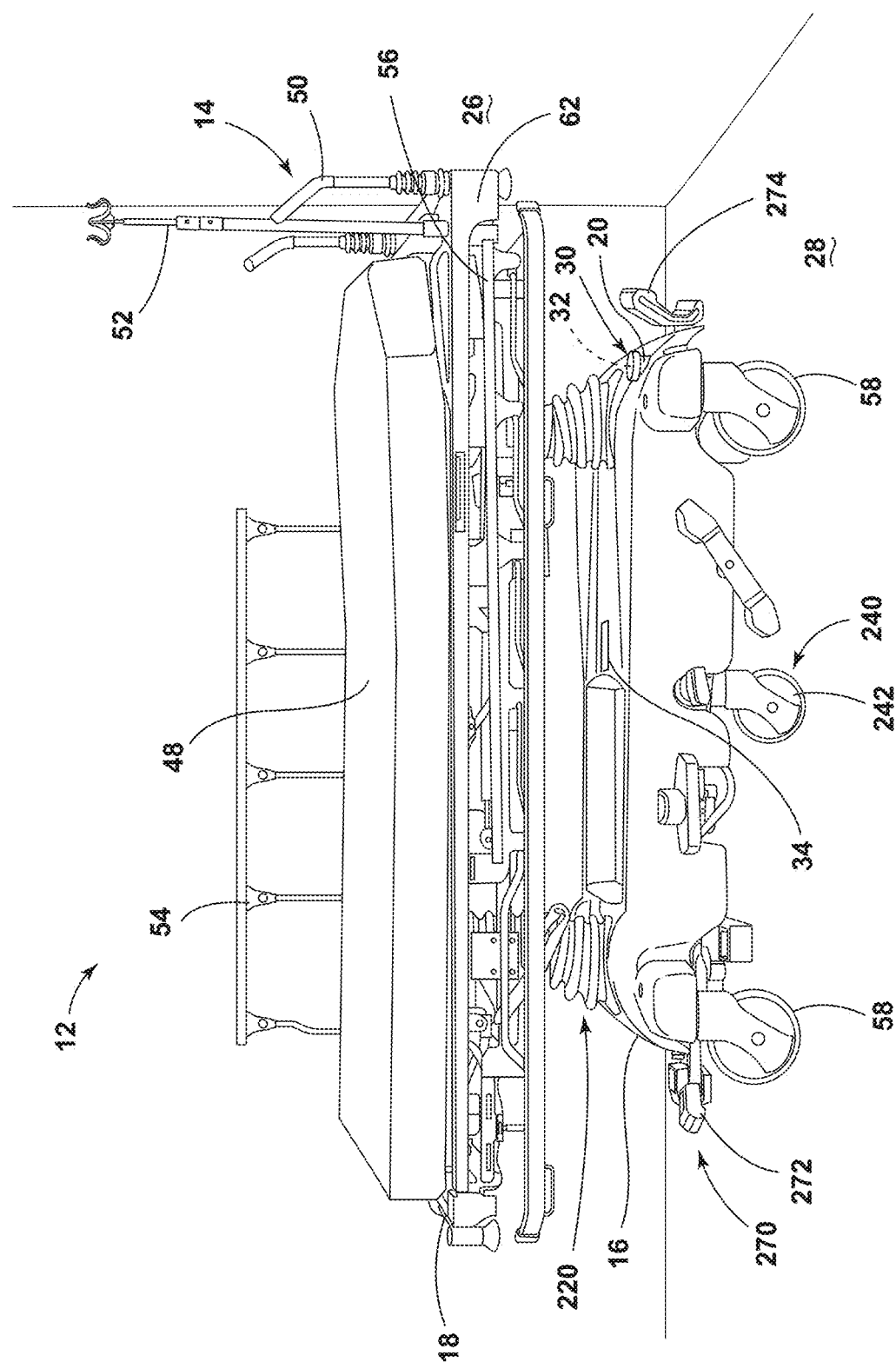
FIG. 9 is a side perspective view of a patient support apparatus with a drive wheel, according to the present disclosure.
Figure 10A:
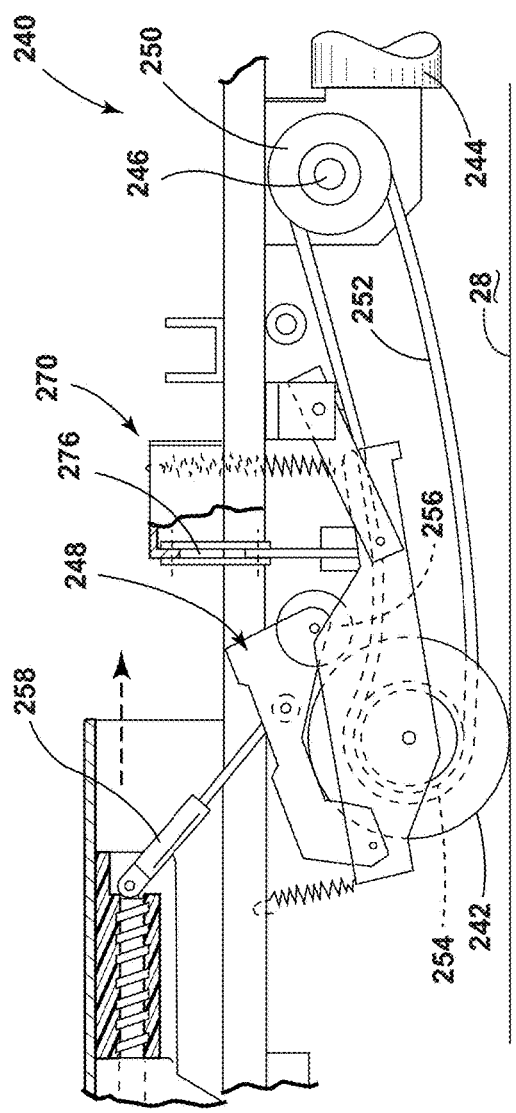
FIG. 10A is a side elevational view of a drive system for a patient support apparatus with a drive wheel in a manual mode of operation, according to the present disclosure.
Figure 10B:
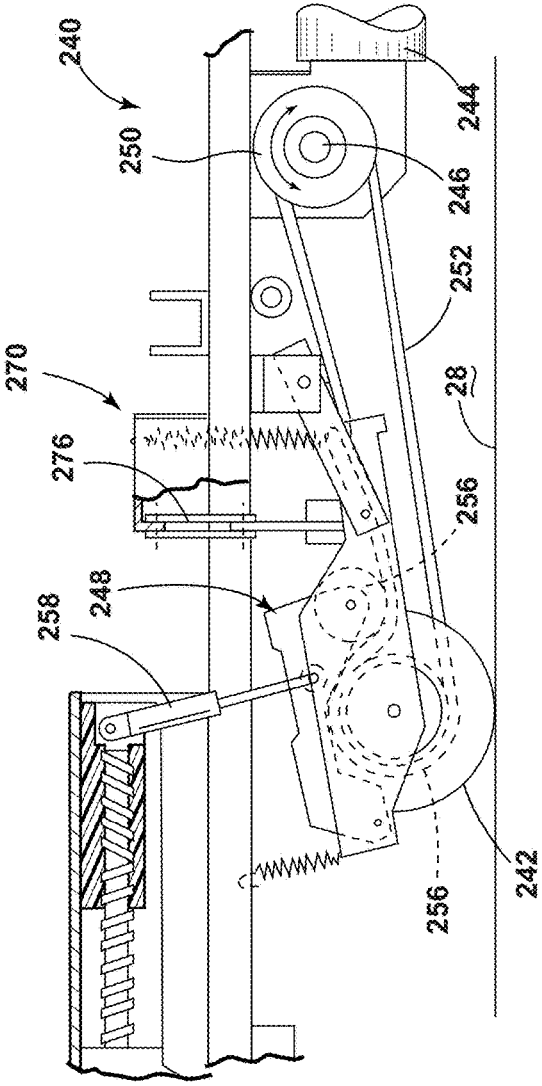
FIG. 10B is a side elevational view of the drive system of FIG. 10A with the drive wheel in a power drive mode.

Referring now to FIGS. 9-10B, the rechargeable battery 20 may power a drive system 240 of the patient support apparatus 14 that has a drive wheel 242. The drive wheel 242 may be a fifth wheel centrally located and coupled to the base frame 16 of the patient support apparatus 14. The drive wheel 242 is configured to assist the caregiver in steering the patient support apparatus 14 by providing a central pivot point about which the patient support apparatus 14 is to turn.

The drive wheel 242 is operably coupled with a motor 244. The motor 244 is generally a variable speed, bidirectional motor 244 that has a rotatable output shaft 246. A selectively engageable clutch 248 selectively couples the motor 244 to the drive wheel 242 when the clutch 248 is engaged. In the illustrated example, the clutch 248 includes a drive pulley 250 coupled to the output shaft 246 of the motor 244 and an axle of the drive wheel 242. A belt 252 extends between the drive pulley 250 and a follower or driven pulley 254 operably coupled with the drive wheel 242. An idler 256 is operably coupled to the base frame 16 via an actuator 258. The idler 256 is adjusted by the actuator 258 relative to the belt 252. The idler 256 may be spaced apart from the belt 252, as illustrated in FIG. 10A, or may press into the belt 252 to put the belt 252 under tension, as illustrated in FIG. 10B.

Referring still to FIGS. 9-10B, the drive system 240 operates to propel the patient support apparatus 14 along the floor surface 28. The drive wheel 242 facilitates steering of the patient support apparatus 14 and drives the patient support apparatus 14 along the floor surface 28 in a power drive mode. The drive system 240 may operate in a manual drive mode of operation. In the manual drive mode, as illustrated in FIG. 10A, the idler 256 is spaced from the belt 252 and the drive wheel 242 is free to rotate when the patient support apparatus 14 is manually pushed. The drive system 240 may also operate in a power drive mode of operation. In the power drive mode, as illustrated in FIG. 10B, the idler 256 is pressed against the belt 252 to transfer rotation from the motor 244 to the drive wheel 242 to propel the patient support apparatus 14.

The drive wheel 242 may be operably coupled with an actuator or a link assembly 276 that operates to adjust the drive wheel 242 relative to the floor surface 28. The drive wheel 242 may be adjusted away from the floor surface 28 to provide space for equipment to be disposed below the base frame 16. The drive wheel 242 may engage the floor surface 28 when in the manual drive mode and the power drive mode. Alternatively, the drive wheel 242 may be adjusted away from the floor surface 28 when in the manual drive mode.

Referring still to FIG. 9, as well as FIGS. 11A and 11B, a brake system 270 of the patient support apparatus 14 may be manually controlled, automatically controlled, or a combination thereof. As best illustrated in FIG. 9, the manual brake system 270 of the patient support apparatus 14 includes a brake pedal 272 coupled to the base frame 16 on the foot end. A brake-steer butterfly pedal 274 is coupled to the base frame 16 on the head end 62 of the base frame 16 to control both braking of the wheels 58 and releasing the brakes of the wheels 58.

The brake system 270 may operate in conjunction with the drive system 240. The brake system 270 is operably coupled with the motor 244 and the drive wheel 242. The brake system 270 may operate the drive wheel 242, as well as any other wheels 58, in a dynamic braking mode. When the controller 36 detects that power supplied to the motor 244 is at or above a predetermined threshold, the drive wheel 242 operates in the power drive mode. When the power is below the predetermined threshold, the drive wheel 242 operates in the dynamic braking mode. The automatic brake system 270 of the patient support apparatus 14 may be powered by the rechargeable battery 20.

In examples with the dynamic braking mode, the controller 36 includes a relay 278 with a movable contact 280, which provides electrical communication between pins P1, P2 when a sufficient current passes through a coil 282. The contact 280 is moved toward the pin P1 by the energized coil 282 against a biasing member, which causes the contact 280 to be drawn toward pin P3, as illustrated in FIG. 11A. The contact 280 of the relay 278 disconnects pins P1, P2 and provides electrical communication between the pins P2, P3 when the current through the coil 282 drops below a predetermined value, as illustrated in FIG. 11B.

The relay 278 is configured to open and connect pins P2 and P3 when a predetermined voltage is applied to the motor 244. The relay 278 functions to switch the motor 244 between the driving mode, as illustrated in FIG. 11A, and the dynamic braking mode, as illustrated in FIG. 11B. In the driving mode, the relay 278 connects power leads 284, 286 of the motor 244 to the rechargeable battery 20, thereby supplying power for driving the motor 244, which consequently causes the drive wheel 242 to drive the patient support apparatus 14. In the braking mode, the relay 278 disconnects the power lead 286 from the motor 244 and instead shorts the power leads 284, 286 through the contact 280. In examples where the motor 244 includes a permanent magnet, shorting the power leads 284, 286 causes the motor 244 to act as an electronic brake, resulting in the drive wheel 242 resisting movement of the patient support apparatus 14. An override switch 288 may be provided to prevent the motor 244 from operating as the electronic brake.

Figure 12:
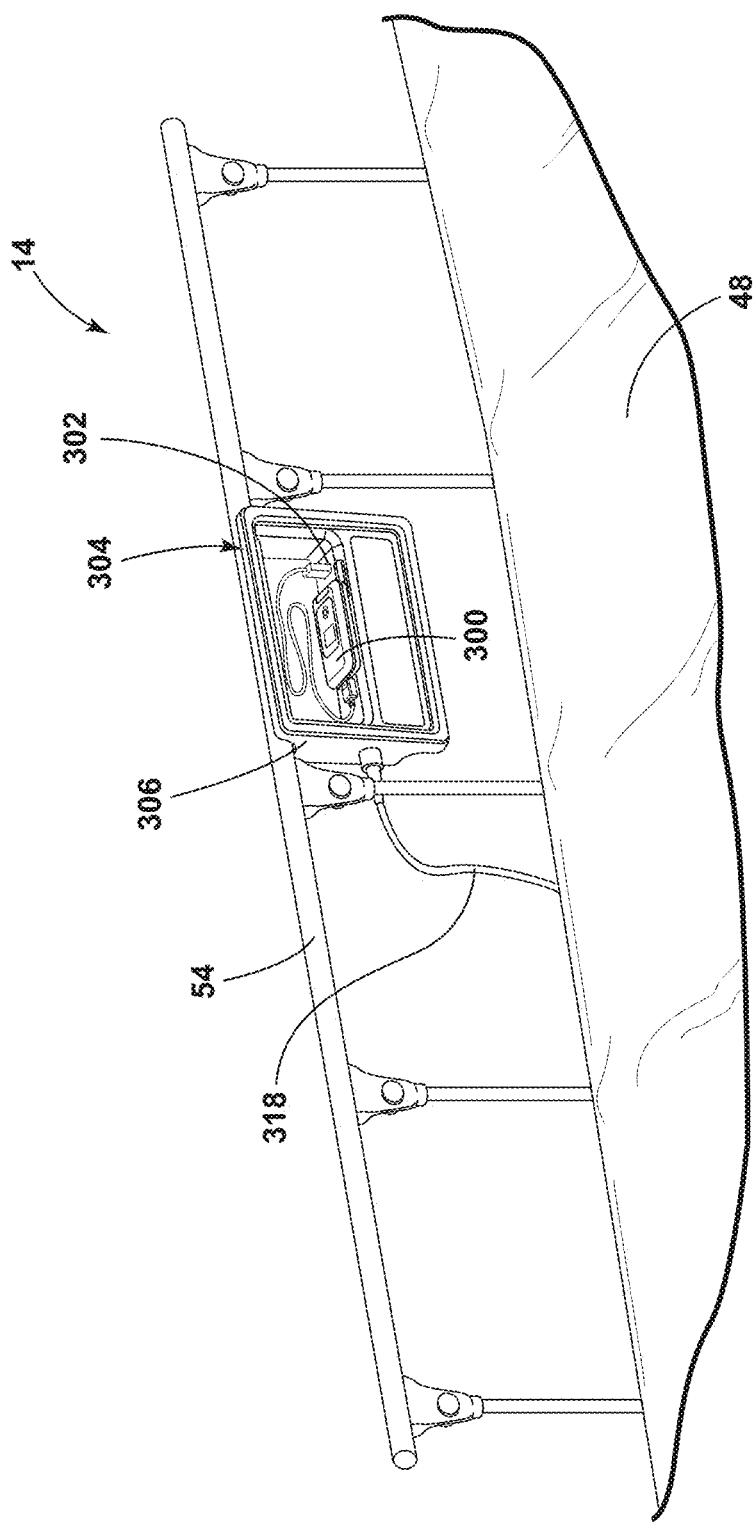
FIG. 12 is a front perspective view of an accessory assembly coupled to a siderail of a patient support apparatus, according to the present disclosure.
Figure 13:
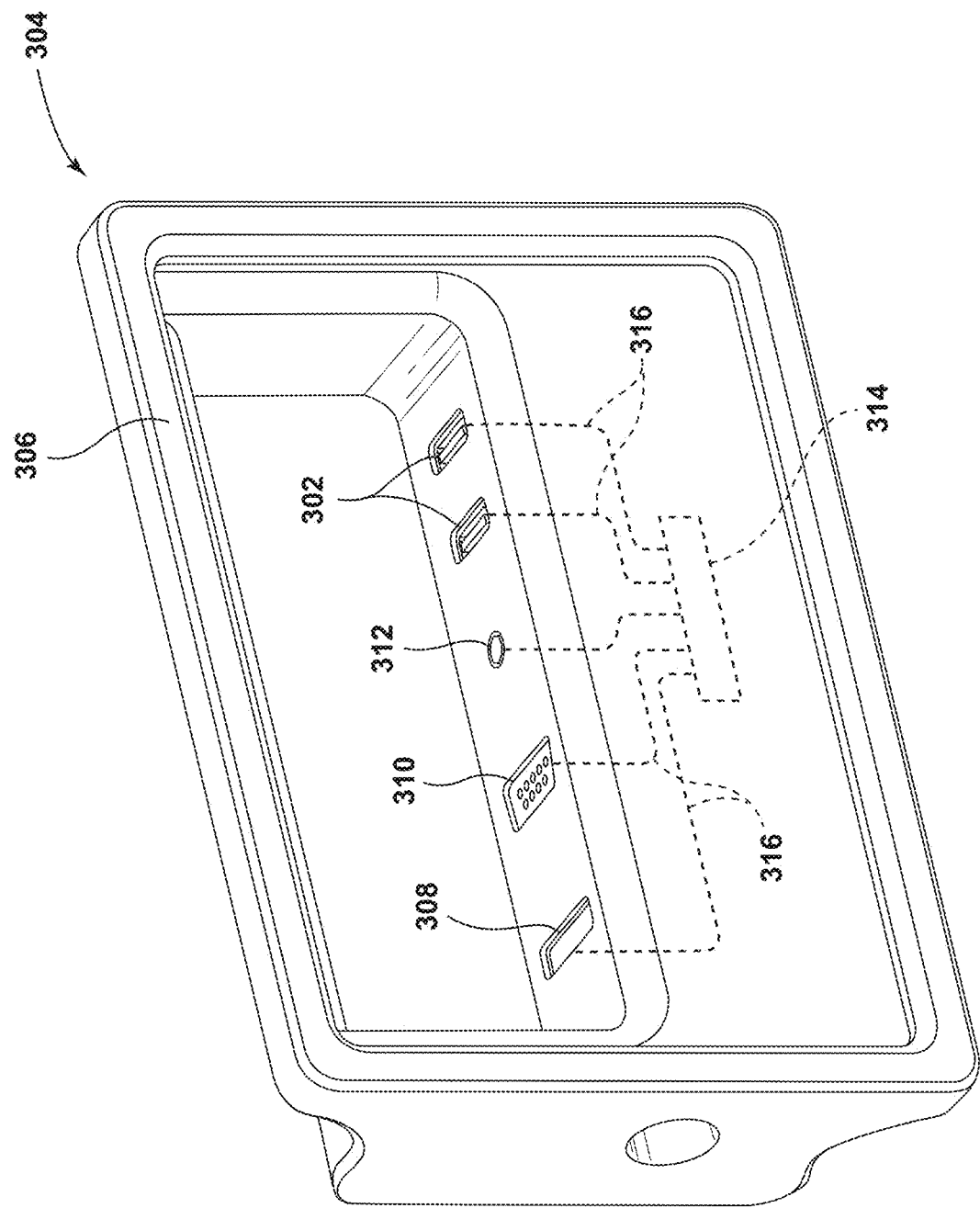
FIG. 13 is a front perspective view of the accessory assembly of FIG. 12 with the remote device removed.

Referring to FIGS. 12 and 13, the rechargeable battery 20 may provide power to personal remote devices 300 through charger ports 302 in an accessory assembly 304 coupled to at least one of the siderail assemblies 54, 56. The personal remote device 300 may be any type of device, including, but not limited to a phone, a tablet, a wearable device, a computer, a laptop, etc. The accessory assembly 304 generally has a housing 306, which is illustrated in the example of FIG. 12 as being coupled to the siderail assembly 54. The patient may connect a power cord for the personal remote device 300 into the charger port 302 and the rechargeable battery 20 may power or charge the personal remote device 300.

As best illustrated in FIG. 13, the patient support apparatus 14 may include one or more types of charger ports 302 or other external device interfaces 308, 310, 312. Each charger port 302 and external device interface 308, 310, 312 is coupled to circuitry 314 via wires or cables 316 and can facilitate communication of data or power between the accessory assembly 304 and the personal remote device 300. Additionally, the accessory assembly 304 may be selectively coupled to one of the siderail assemblies 54 and also coupled to the patient support apparatus 14 via an electrical connector 318 to provide data and power communication between the patient support apparatus 14 and the accessory assembly 304. The controller 36 generally controls communication of the data or power between the external device interfaces 308, 310, 312, the charger ports 302, the personal remote device 300, and the patient support apparatus 14. Further, the electrical connector 318 may provide power from the rechargeable battery 20 to the accessory assembly 304 and the personal remote device 300.

Figure 14:
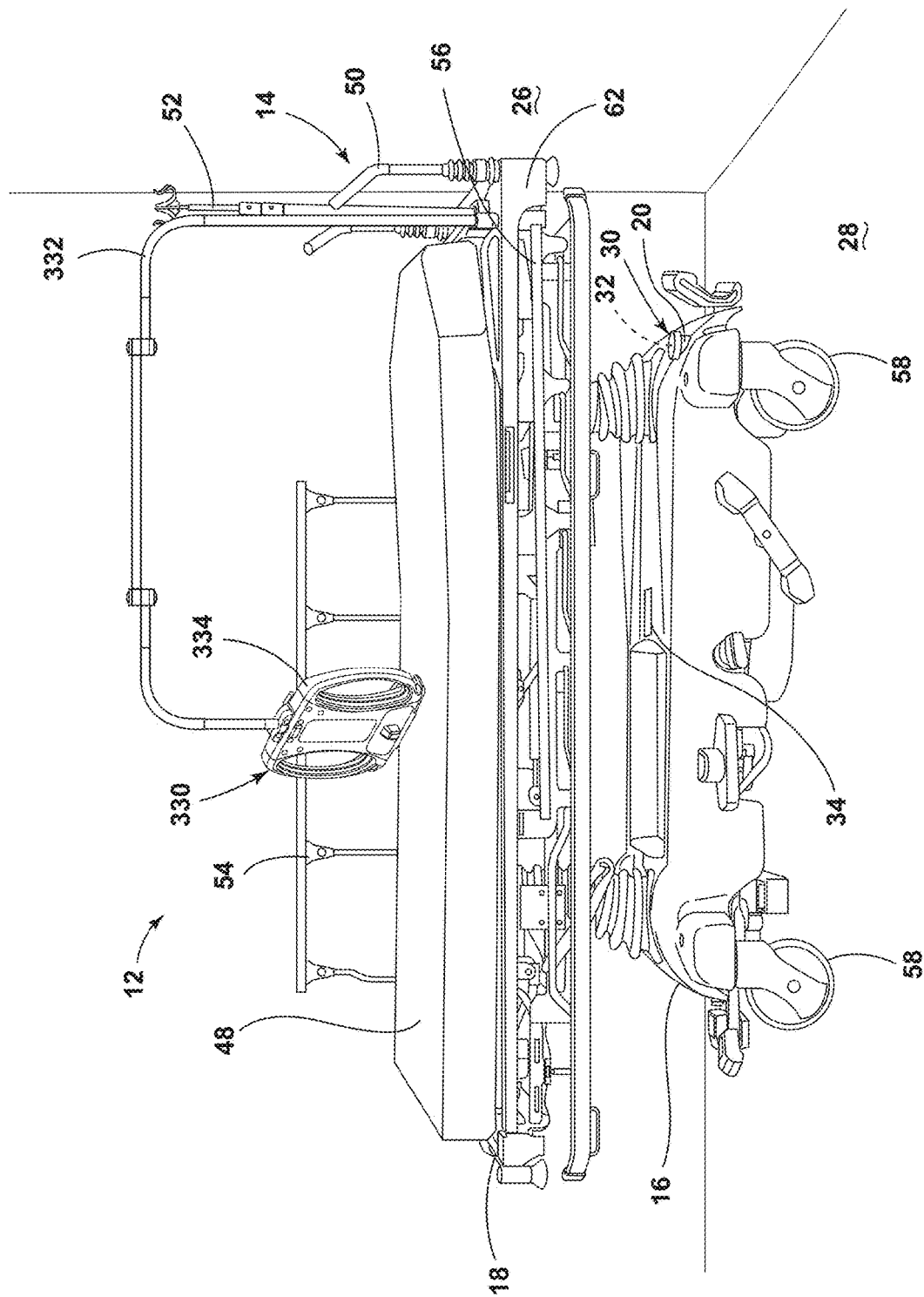
FIG. 14 is a side perspective view of a patient support apparatus that includes a pendant, according to the present disclosure.
Figure 15B:
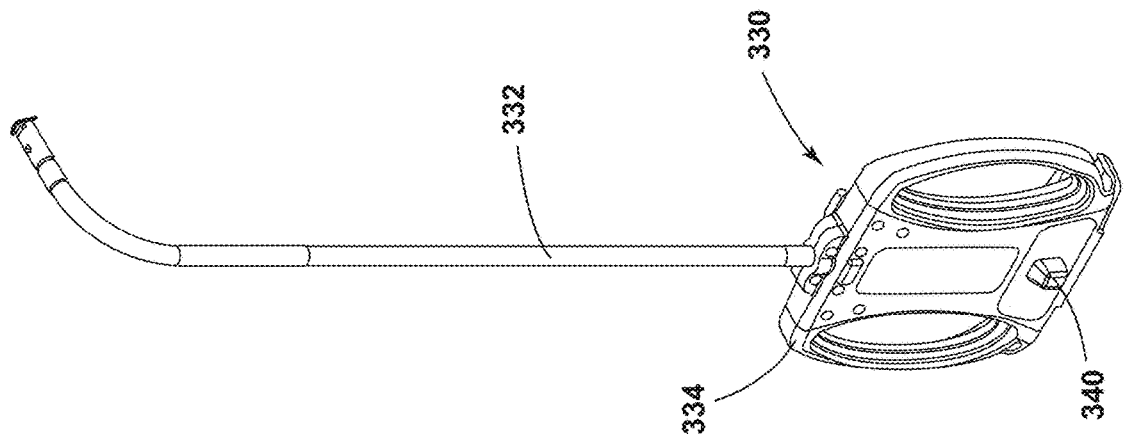
FIG. 15B is a rear perspective view of the pendant of FIGS. 15A.
Figure 15A:
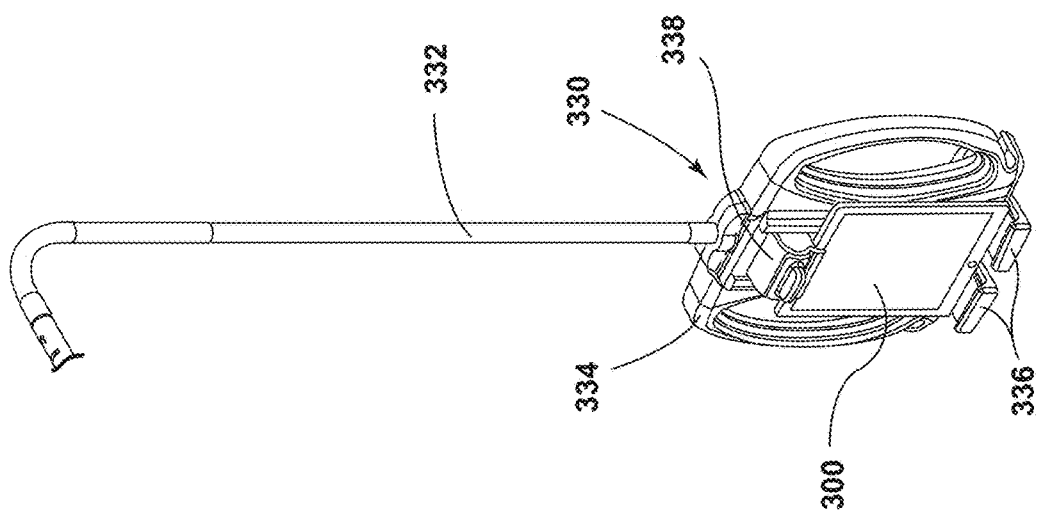
FIG. 15A is a front perspective view of the pendant of FIG. 14 separate from the patient support apparatus.

Referring to FIGS. 14-15B, a device housing or a pendant 330 may be coupled to the patient support apparatus 14 via an arm 332. The pendant 330 generally includes components powered by the rechargeable battery 20. An electric connection generally extends from the patient support apparatus 14, through the arm 332, and to the pendant 330 for powering the pendant 330. The arm 332 is generally at least partially flexible to position the pendant 330 in various positions relative to the patient support apparatus 14 for optimal view of the pendant 330 by the patient. Additionally or alternatively, the arm 332 may include multiple independently movable segments that assist in positioning the pendant 330 in the selected location.

The pendant 330 includes a support structure 334 for retaining or housing the personal remote device 300. The personal remote device 300 is disposed on a shelf 336 and retained by a latch 338. The shelf 336 and the latch 338 are adjustable to retain personal remote devices 300 of various sizes and shapes. Generally, the pendant 330 holds the personal remote device 300 and provides a convenient location for storage of the personal remote device 300, as well as for entertainment purposes (e.g., for viewing a display of the personal remote device 300). The pendant 330 includes a charger port 340 for charging the personal remote device 300 disposed on the support structure 334 through power supplied by the rechargeable battery 20. It is also contemplated that the support structure 334 includes an integrated display that is powered by the rechargeable battery 20.

Figure 16:
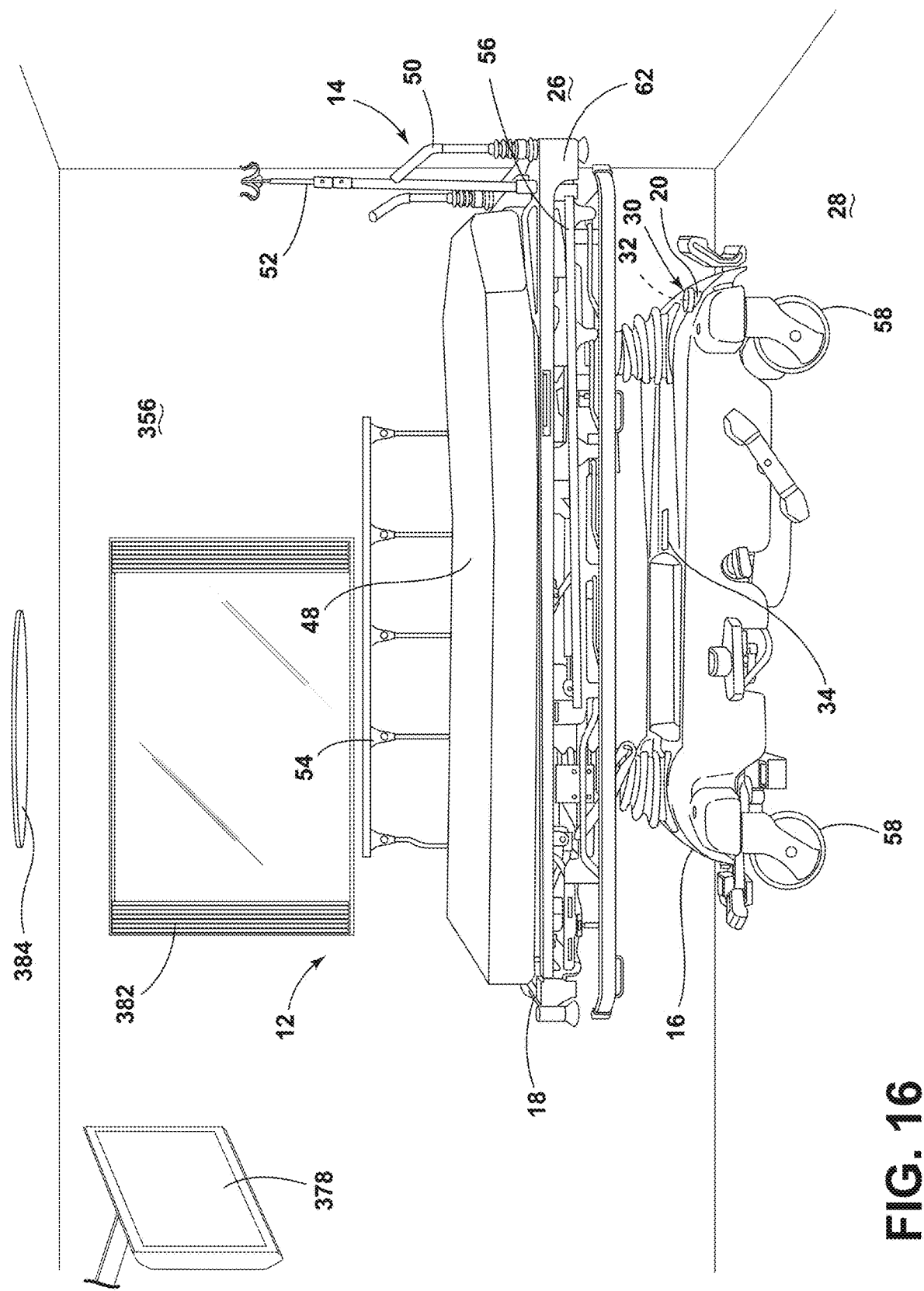
FIG. 16 is a partial side perspective view of a room environment that includes a patient support apparatus, according to the present disclosure.
Figure 17:
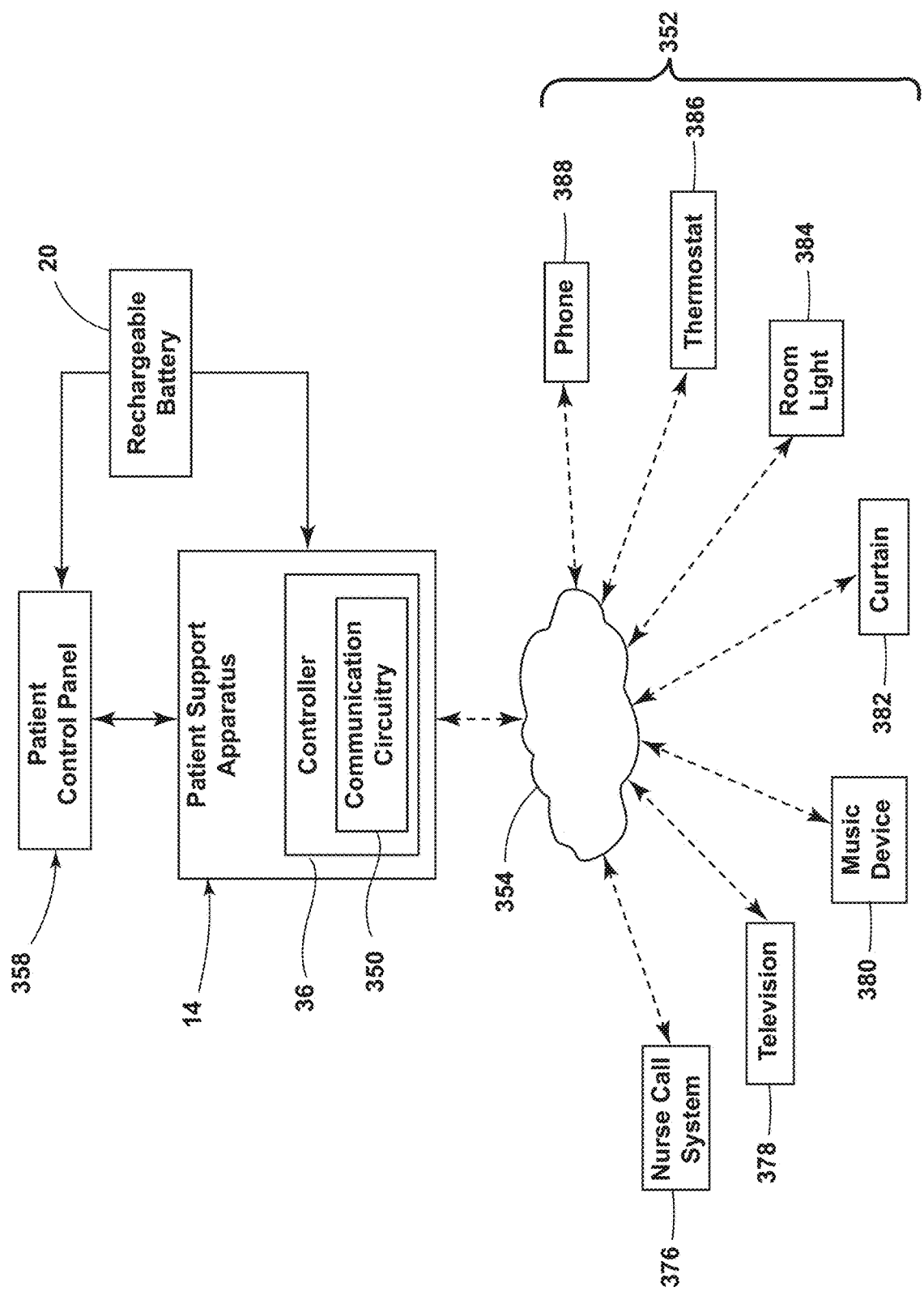
FIG. 17 is a block diagram of communication between the patient support apparatus and features in the room environment of FIG. 16.

Referring to FIGS. 16 and 17, the rechargeable battery 20 provides power to the controller 36, which includes communication circuitry 350 configured to communicate with a remote device 352, which may include handheld remote devices 352 (e.g., phones, tablets, wearable electronic devices, etc.) and remote servers (e.g., cloud servers, Internet-connected databases, computers, etc.) via a communication interface 354. The communication interface 354 may be a network having various wired or wireless communication mechanisms. Exemplary communication networks include wireless communication networks, such as, for example, a Bluetooth® transceiver, a ZigBee® transceiver, a Wi-Fi transceiver, an IrDA transceiver, an RFID transceiver, etc. The controller 36 and the remote device 352 may include circuitry configured for bidirectional communication. Additional exemplary communication networks include local area networks (LAN) or wide area networks (WAN), including the Internet and other data communications services. The controller 36 and the remote device 352 may communicate by any suitable technology for exchanging data. The remote device 352 may be any personal device, any device or system associated with the medical facility 12, or other separate devices.

The controller 36 may be in communication with various comfort and treatment systems via wired or wireless communication. For example, the patient may control various features of a room environment 356 via the patient support apparatus 14, the user interface 144, or another control panel. One or both of the patient support apparatus 14 and the user interface 144 includes a patient control panel 358 for receiving an input from the patient. The patient control panel 358 is operably coupled with the controller 36. The patient control panel 358 generally includes one or more buttons, knobs, or icons 360 that are selectable by the patient, the caregiver, or both. The icons 360 correspond with various features for the patient and the caregiver. For example, the icons 360 may include a bed control icon 362, a nurse call icon 364, a television control icon 366, a music control icon 368, an environment control icon 370, an internet icon 372, a phone icon 374, etc. These icons 360 are merely exemplary and are not meant to be limiting. Any features within the room environment 356 may be controlled through the patient control panel 358 without departing from the teachings herein.

Figure 18:
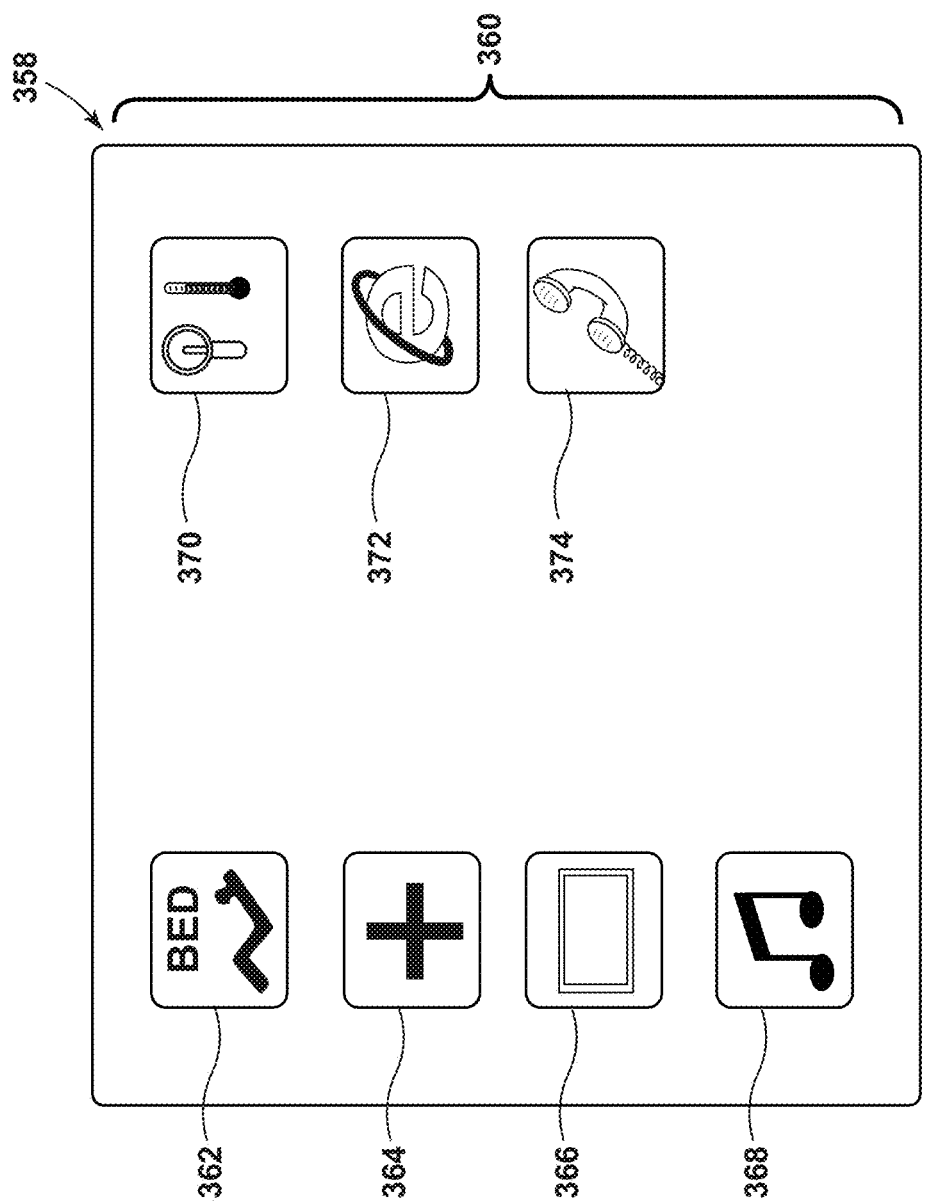
FIG. 18 is a schematic view of a user interface with selectable icons relating to the features in the room environment of FIG. 16.

With regard to the exemplary icons 360 illustrated in FIG. 18, the bed control icon 362 allows the patient to adjust the upper frame 18 or the adjustable frame 200 of the patient support apparatus as previously described herein. The nurse call icon 364 is associated with a nurse call system 376 that alerts the caregiver that the patient is in need of assistance, as discussed in greater detail herein.

The television control icon 366 allows the patient to control a television 378 within the room environment 356 that is communicatively coupled with the patient control panel 358. When selected, the television control icon 366 provides a television control screen that allows for the patient to control various aspects of the television 378, including, but not limited to, turning the television 378 on or off, changing a channel, changing a volume, etc. The music control icon 368 allows the patient to control a music device 380 operably coupled with the patient control panel 358. Selection of the music control icon 368 provides a menu that allows the patient to control various aspects of the music device 380, including, changing a station, changing a volume, scanning, etc.

Selection of the environment control icon 370 allows the patient to control features of the room environment 356 including a curtain 382, a room light 384, a room thermostat 386 (e.g., raise temperature, lower temperature, off, etc.), etc. For example, the patient can adjust the curtain 382 between opened, closed, and partially opened positions. The patient may also adjust the room light 384 between on or off states, as well as dimmed states. Additionally or alternatively, the patient may raise or lower a temperature within the room environment 356. The adjustment of the temperature may be within a predefined range selected by the caregiver or the overall medical setting. Selection of the Internet icon 372 allows the patient to access the Internet, and selection of the phone icon 374 may allow the patient control panel 358 to be utilized as a telephone 388 or controls the telephone 388 within the room environment 356. The patient control panel 358 is generally powered by the rechargeable battery 20 and allows the patient to control various features within the room environment 356 through wired or wireless communication.

Figure 19:
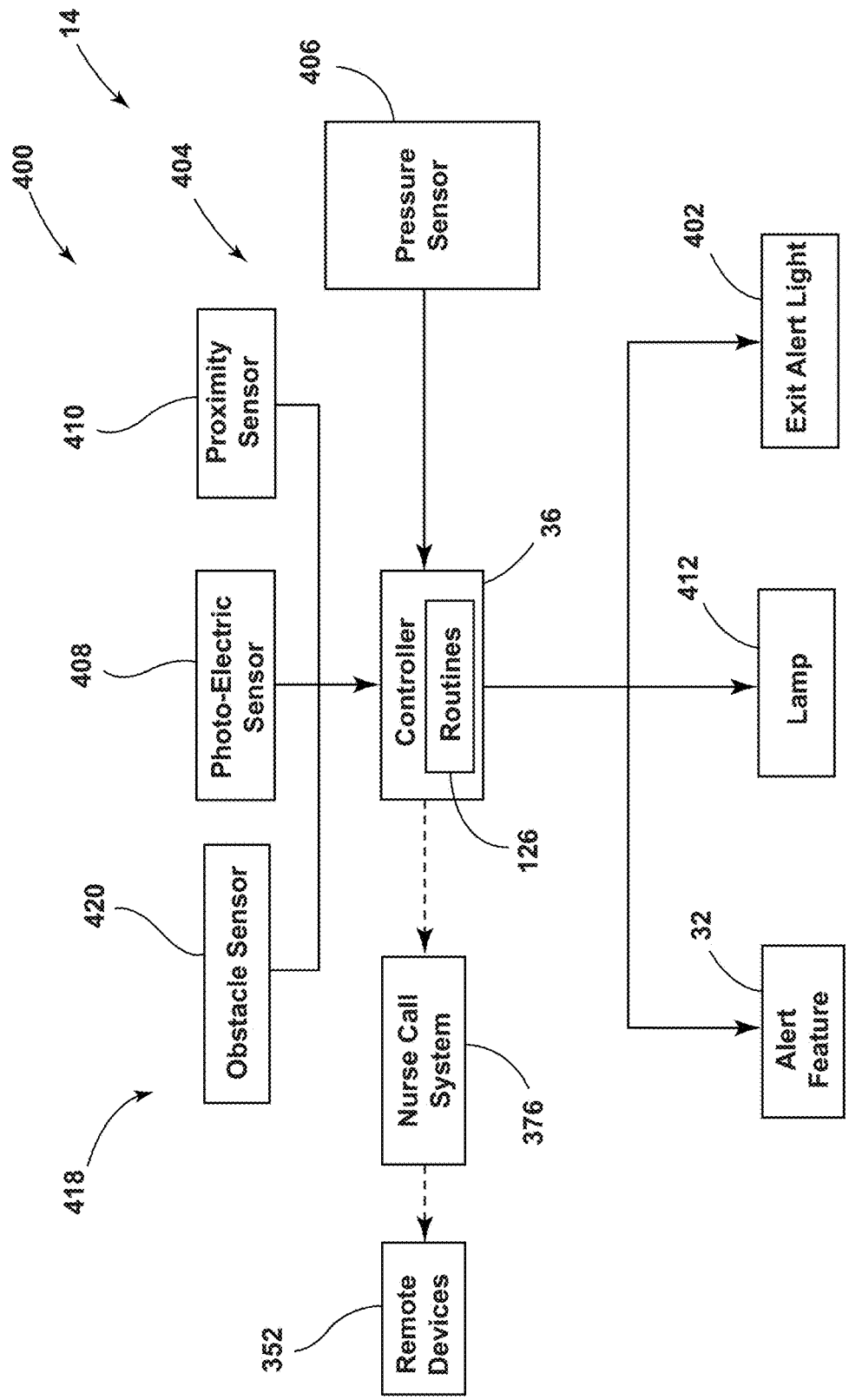
FIG. 19 is a block diagram of a patient monitoring system and an obstacle detection system for a patient support apparatus, according to the present disclosure.

Referring still to FIGS. 16 and 17, as well as to FIG. 19, the rechargeable battery 20 may also power a patient monitoring system 400. The patient monitoring system 400 may incorporate a bed exit or fall risk protocol, as well as other monitoring of the patient on the patient support apparatus 14. The patient monitoring system 400 includes an exit alert light 402 disposed on the patient support apparatus 14. The exit alert light 402 is activated by the controller 36 to illuminate when the patient is attempting to exit the patient support apparatus 14. The patient support apparatus 14 includes one or more sensors 404 operably coupled to the upper frame 18, the base frame 16, or a combination thereof. The sensors 404 include any type of force, weight, or pressure sensor 406. The pressure sensors 406 generate a load signal that is communicated to the controller 36 and which indicates the presence or movement of the patient on the patient support apparatus 14. The presence or movement may be monitored in accordance with the fall risk protocol or other protocols, where the patient is not to exit the patient support apparatus 14 without the assistance of the caregiver.

The patient support apparatus 14 may also include photoelectric sensors 408 that detect an intensity of light within the environment around the patient support apparatus 14. The photoelectric sensors 408 communicate a light intensity signal to the controller 36. When the controller 36 determines that the movement of the patient on the patient support apparatus 14 is at or above a predetermined movement threshold, indicating the patient may exit and that the light intensity is at or below a predetermined intensity threshold, the controller 36 activates the exit alert light 402 to illuminate the surrounding area.

The illumination of the exit alert light 402 may act as a visual indicator to the caregiver that the patient may attempt to exit the patient support apparatus 14 while providing light to minimize risks associated with exiting the patient support apparatus 14 with lower visibility. If the light intensity is at or above the predetermined threshold, the controller 36 may not activate the exit alert light 402 or may deactivate an illuminated exit alert light 402. The patient support apparatus 14 may also include proximity sensors 410 to detect a person, such as the caregiver, proximate the patient support apparatus 14, which is communicated to the controller 36. When the proximity sensor 410 detects a person, the controller 36 may not illuminate the exit alert light 402 as the caregiver is present to assist the patient exiting the patient support apparatus 14.

Referring still to FIGS. 16, 17, and 19, in various examples, the patient monitoring system 400 may be utilized when the fall risk protocol (e.g., a routine 126) is activated. In such examples, the patient may not exit the bed (e.g., the patient support apparatus 14) without the assistance of a caregiver due to a heightened risk of a fall hazard. When the fall risk protocol is activated, the controller 36 monitors the movement of the patient and the intensity of the light in the surrounding environment. If the movement of the patient is indicative of an intent to exit the patient support apparatus 14, the controller 36 activates the exit alert light 402 to illuminate the area surrounding the patient support apparatus and minimize the risk of injury. Additionally, the controller 36 communicates with the alert feature 34 and the nurse call system 376 to alert the caregiver that the patient is attempting to exit the patient support apparatus 14.

The controller 36 generally includes one or more routines 126 relating to monitoring the patient with the patient monitoring system 400. The controller 36 monitors the movement of the patient by monitoring the weight distribution among the pressure sensors 406 relative to predetermined movement thresholds stored in the memory 124. Additionally or alternatively, the controller 36 may determine a center of gravity of the patient using the pressure sensors 406. The controller 36 compares the detected measurements obtained by the pressure sensors 406 with the predetermined center of gravity region. If the pressure is sensed outside the predetermined center of gravity region, the patient may be exiting the patient support apparatus 14. In another example, the controller 36 may compare subsequent load signals to determine the change in position of the patient. Additional methods of detecting the movement of the patient on the patient support apparatus 14 may be utilized without departing from the teachings herein.

The nurse call system 376 is also configured to detect alarm conditions related to the patient, the status of the patient support apparatus 14, the status of the rechargeable battery 20, various therapies, or other aspects, and send an alert to other remote devices 352. The remote device 352 may display information about the patient, such as room number, name, and alarm condition of the monitored equipment or the patient. When the nurse call system 376 sends an alert, the caregiver can answer the call through the remote device 352. The remote device 352 may be included in, or associated with, a master nurse call station of the medical facility 12. The nurse call system 376 allows the patient to manually place a nurse call or conveys an automatic alarm through one of the various systems of the patient support apparatus 14.

Referring still to FIG. 19, in an additional example, the patient support apparatus 14 may include a lamp 412 operably coupled to one of the siderail assemblies 54, 56, the pendant 330, or other locations on the patient support apparatus. The lamp 412 may provide area lighting around the patient support apparatus 14, may be configured as a reading lamp, or a combination thereof. The lamp 412 may be used in conjunction with and independently of the patient monitoring system 400.

Referring still to FIG. 19, as well as to FIGS. 20-22, the rechargeable battery 20 may power an obstacle detection system 418 for the patient support apparatus 14. The obstacle detection system 418 includes a plurality of obstacle sensors 420 disposed on the patient support apparatus 14, which may be proximity sensors or other types of sensors. The obstacle detection system 418 is in communication with the user interface 144 associated with the patient support apparatus 14. In various examples, the obstacle sensors 420 are disposed on at least one of the lift system 220, the base frame 16, and the upper frame 18. The obstacle sensors 420 are configured to detect the presence of an object or obstacle within an articulation path of the patient support apparatus 14. For example, when the obstacle sensors 420 detect an object in a space between the upper frame 18 and the base frame 16, the controller 36 prevents movement of the upper frame 18 and the base frame 16 into the space to prevent a collision with the object.

The obstacle sensors 420 communicate an obstacle signal to the controller 36, and the controller 36 activates a graphical alert 422 on the display 146 of the user interface 144. The graphical alert 422 illustrates the location of the obstacle relative to the patient support apparatus 14. For example, as illustrated in FIG. 20, the obstacle is detected by the foot end of the patient support apparatus 14. As illustrated in FIG. 21, two obstacle locations are detected, with an obstacle detected at the foot end and a left side of the patient support apparatus 14. As illustrated in FIG. 22, the obstacles are detected at the foot end and a right side of the patient support apparatus 14. The graphical alert 422 illustrates the location of the obstacle to the caregiver, allowing the caregiver to remove the obstacle and, thereby, allow the patient support apparatus to move along the selected articulation path. It is contemplated that the graphical alert 422 may be communicated to other locations, such as the remote devices 352. Other types of alerts indicating sensed obstacles are also contemplated without departing from the teachings herein.

Figure 23:
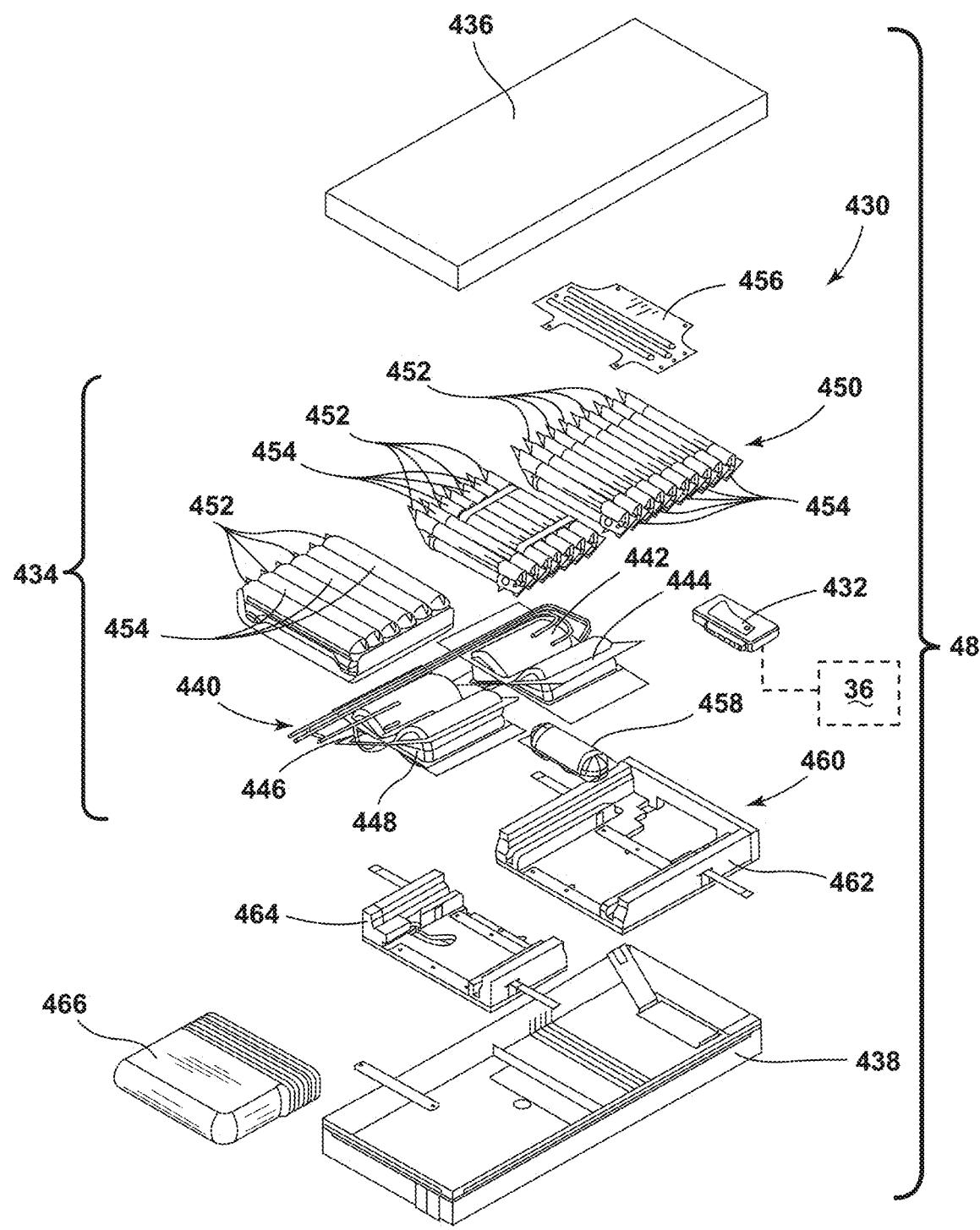
FIG. 23 is a perspective exploded view of a pneumatic system for a patient support apparatus, according to the present disclosure.

Referring to FIG. 23, as previously discussed, the controller 36 may be in communication with various comfort or treatment systems that are also powered by the rechargeable battery 20. For example, the rechargeable battery 20 may power a pneumatic system 430 within the mattress 48. The rechargeable battery 20 may provide power to a pump 432, which adds or removes fluid from each bladder 434 of the pneumatic system 430. The amount of fluid within each bladder 434 adjusts the firmness of the mattress 48. Additionally, the bladders 434 may be used for pressure therapy, for example for pressure ulcer prevention. The bladders 434 may be adjusted in a certain pattern to apply pressure therapy or other treatments to the patient and the patient support apparatus 14.

In various examples, the mattress 48 includes an upper cover 436 and a base cover 438 that enclose the pneumatic system 430. The pneumatic system 430 may provide one or more types of treatment to the patient. For example, the pneumatic system 430 powered by the rechargeable battery 20 may be utilized to provide continuous lateral rotation therapy for the patient on the patient support apparatus 14. The bladders 434 may include rotation bladders 440 within the mattress 48. The rotation bladders 440 may be inflated in a certain pattern to provide a gentle, side-to-side movement of the patient to aid in the prevention and treatment of pulmonary and other health complications related to immobility, as well as treat or prevent pressure ulcers.

In the illustrated configuration, the rotation bladders 440 include first and second turn bladders 442, 444 arranged adjacent to third and fourth turn bladders 446, 448. The first and second turn bladders 442, 444 are arranged under a torso of the patient when the patient is lying on the patient support apparatus 14 and operate to turn the torso along a longitudinal axis in response to the inflation of one of the first and second turn bladders 442, 444. The third and fourth turn bladders 446, 448 are arranged under a seat or thigh of the patient and operate to turn the legs of the patient along the longitudinal axis in response to the inflation of one of the third and fourth turn bladders 446, 448. For example, to rotate the patient to the right, the second and fourth turn bladders 446, 448 are inflated. The first and third turn bladders 442, 446 may remain in a current state or may deflate. As illustrated in the example of FIG. 23, the first and second turn bladders 442, 444 are in fluid communication with the third and fourth turn bladders 446, 448 for concurrent inflation and deflation. However, each set of rotation bladders 440 may operate independently. Additional rotation bladders 440 may be included in the pneumatic system 430 without debating from the teachings herein.

The rotation bladders 440 operate to adjust the patient between a center position, in which the patient is lying on his or her back, and lateral positions, in which the patient is lying on his or her right or left side. The controller 36 may control the pneumatic system 430 to vary a number of turns, a pause time in each position, a duration of the continuous lateral rotation therapy, etc. to provide customized treatment for the patient. The amount of pressure provided by each rotation bladder 440 may be based on a detected or input weight of the patient. The continuous lateral rotation therapy may be initiated through the user interface 144, the remote device 352, or other aspects of the charging system 10.

Referring still to FIG. 23, the pneumatic system 430 may include support bladders 450 arranged over the rotation bladders 440. The support bladders 450 support the patient lying on the mattress 48. Each of the support bladders 450 may include one or more cells that may be concurrently or independently adjusted between inflated and deflated conditions. The support bladders 450 may also be utilized to provide alternating pressure therapy to the patient. When providing alternating pressure therapy, a first set of support bladders 452 are in fluid communication, and a second set of support bladders 454 are in fluid communication. The first set of support bladders 452 and the second set of support bladders 454 are arranged in an alternating pattern. Accordingly, the first set of support bladders 452 and the second set of support bladders 454 are separately inflated, maintained, or deflated in a pattern to relieve pressure points by cyclically dropping or elevating a pressure within one of the first set of support bladders 452 and the second set of support bladders 454. The controller 36 may include alternating pressure therapy protocols that include at least frequency, duration, pattern, and intensity of the therapy. The alternating pressure therapy may be initiated and adjusted (e.g., frequency, duration, intensity, etc.) via the user interface 144, the remote device 352, or other aspects associated with the charging system 10.

Additionally or alternatively, the pneumatic system 430 powered by the rechargeable battery 20 may be utilized to provide percussion and vibration therapies to the patient on the patient support apparatus 14. The percussion and vibration therapies may be conducted separately or together as sequential treatments. Percussion and vibration therapy (PVT) bladders 456 are disposed over the support bladders 450. While illustrated in FIG. 23 proximate the head end of the mattress 48, the PVT bladders 456 may be disposed in other locations in the mattress 48, or alternatively, multiple sets of PVT bladders 456 may be disposed in the mattress 48. The PVT bladders 456 provide percussion or vibration therapies when pressure in the PVT bladders 456 drops and elevates at a rate sufficient to impart a vibration to the patient. For example, percussion or vibration therapy may be applied to a chest region of the patient to aid in breaking down undesired materials within the lungs of the patient.

Referring still to FIG. 23, the percussion and vibration therapies may also be utilized in conjunction with other therapies, such as continuous lateral rotation therapy. The controller 36 may include percussion and vibration protocols that include at least frequency, duration, and intensity of the therapies. The percussion and vibration therapies may be initiated and adjusted (e.g., frequency, duration, intensity, etc.) via the user interface 144, the remote device 352, or other aspects associated with the charging system 10. The percussion and vibration therapies may be utilized to treat or prevent pulmonary or other complications associated with immobility, treat or prevent pressure ulcers, or any additional medical benefits.

The pneumatic system 430 may also be utilized for providing a turn assist for the caregiver. The controller 36 may include a turn assist protocol, which assists the caregiver in turning the patient on the patient support apparatus 14 for linen changes, dressing changes, bedpan placement, back care, and other procedures or treatments. When the turn assist protocol is activated, some or all of the bladders 434 in the mattress 48 are adjusted.

For example, when the patient is to be turned onto his or her right side, the bladders 434 on the left side of the mattress 48 may inflate, consequently rotating the patient. In such an example, the bladders 434 on the right side of the mattress 48 may remain in a current state (e.g., neither inflate nor deflate) or may deflate to further contribute to the rotation of the patient. The turn assist protocol may be initiated through the user interface 144, the remote device 352, or other aspects of the charging system 10. In various examples, certain conditions of the patient support apparatus 14 may be met before the turn assist protocol is initiated. For example, the siderail assembly 54, 56 in the direction the patient is to be turned may be raised before the turn assist protocol is initiated. In such configurations, an alert or message may be provided via the user interface 144, the alert feature 34, or other aspects of the charging system 10 if the condition is not met prior to attempted activation of the turn assist protocol.

The pneumatic system 430 may also include a fill bladder 458 disposed below the support bladders 450 within the mattress 48. The fill bladder 458 may be utilized to fill a gap formed between the support bladders 450 and adjustable frame 200 as the adjustable frame 200 articulates between different positions. As different segments of the adjustable frame 200 move, the fill bladder 458 inflates to fill any gap or space between adjacent segments. It is contemplated that the pneumatic system 430 may have additional components or functions without departing from the teachings herein. It is also contemplated that the pneumatic system 430 may include fewer bladders 434 where each bladder 434 performs multiple functions to provide different therapies.

Additionally or alternatively, the mattress 48 generally includes a shell assembly 460 for retaining the various components of the pneumatic system 430 in a selected position. The shell assembly 460 includes at least first, second, and third shells 462, 464, 466 that retain the bladders 434 in selected regions (e.g., head end, seat, etc.) of the mattress 48. The shell assembly 460 is disposed on the base cover 438 and provides support for the pneumatic system 430. The shell assembly 460 may also assist in positioning or retaining the pump 432. It is contemplated that tubing, manifolds, or other connectors may extend from the pump 432 and through the mattress 48 to connect with each of the bladders 434. The shell assembly 460 may include grooves or other features for guiding the tubing between the pump 432 and the various bladders 434.

Figure 24:
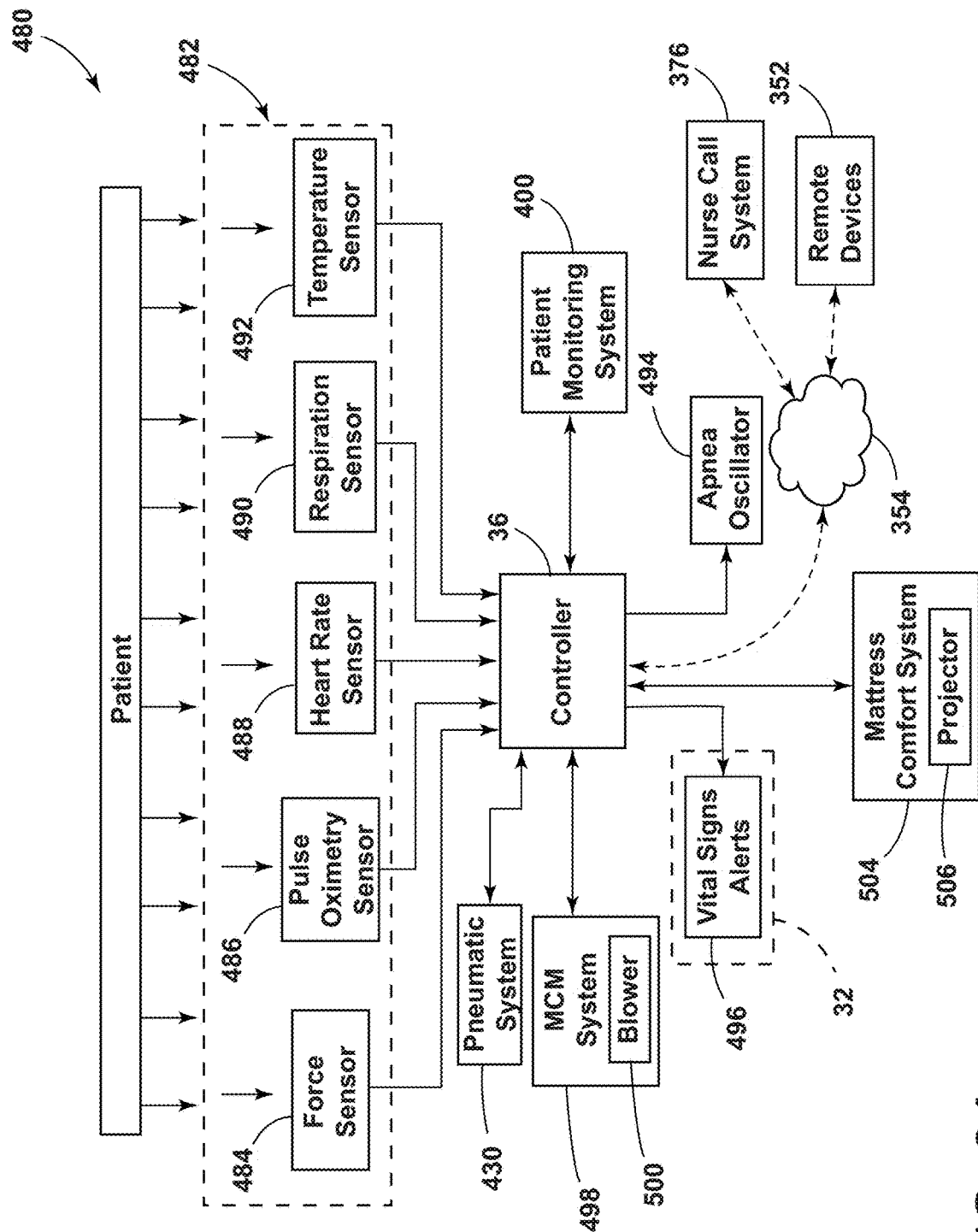
FIG. 24 is a block diagram of a health management system for a patient support apparatus, according to the present disclosure.

Referring to FIG. 24, the rechargeable battery 20 may also power a health monitoring system 480. The health monitoring system 480 generally includes various sensors for monitoring vital signs and other physiological parameters of the patient on patient support apparatus 14. The health monitoring system 480 may monitor one or more physiological parameters, such as core body temperature or skin temperature, pulse rate, heart rate, blood pressure, respiratory rate, body weight, other body signs such as end-tidal $CO_2$, $SpO_2$ (saturation of oxygen in arterial blood flow), and other indicators the physiological state of the patient. The health monitoring system 480 includes physiological sensors 482 for obtaining the physiological and other vital sign data from the patient on the patient support apparatus 14. The physiological sensors 482 are generally coupled with the upper frame 18 or the siderail assemblies 54, 56 of the patient support apparatus. The physiological sensors 482 may be non-contact sensors that are configured to obtain data without direct contact with the patient.

It is also contemplated the physiological sensors 482 may be configured as sensing zones or layers. In such configurations, the physiological sensors 482 are disposed below a mattress cover and within the mattress 48. In non-limiting examples, the sensing zones or layers may be constructed of two conductive layers separated by a semiconductor layer, with electrical connectors extending between the controller 36 and the conductive layers. In additional non-limiting examples, the sensing zones or layers may be constructed of resistive or capacitive film providing a grid or matrix of sensors. It is also contemplated that the physiological sensors 482 may be pressure-strip sensors disposed on the bladders 434 of the pneumatic system 430.

According to various aspects, the physiological sensors 482 may include force sensors 484. The force sensors 484 obtain a weight data of the patient to provide a scale feature to the patient support apparatus 14. This scale feature allows caregivers to weigh patients without the patient leaving the patient support apparatus 14. Certain aspects of the patient support apparatus 14, such as the pneumatic system 430, may be adjusted in response to a weight sensed by the force sensors 484.

Additionally or alternatively, the force sensors 484 and the controller 36 may operate together to sense, monitor, and record the weight of the patient. The controller 36 may communicate the weight data to the remote device 352 where the data can be viewed by the caregiver and stored in the Electronic Medical Records (EMR) of the patient. It is contemplated that the controller 36 may include one or more routines 126 to differentiate the weight of the patient from the weight of different aspects of the mattress 48 or the patient support apparatus 14. The force sensors 484 may also be configured to sense shear forces between the patient and the mattress 48, which can restrict blood flow and contribute to pressure ulcers on the patient. It is also contemplated that the pressure sensors 406 that monitor patient movement may also be utilized to detect the weight of the patient.

The physiological sensors 482 may be utilized as a diagnostic tool to allow the caregiver to monitor the condition of the patient. The physiological sensors 482 may include a pulse oximetry sensor 486. In various examples, the pulse oximetry sensor 486 is included in an oximetry sensing device or "finger clasp" operably coupled with the patient support apparatus 14. The pulse oximetry sensor 486 obtains data relating to blood oxygenation levels of the patient, such as $SpO_2$. The physiological sensors 482 may also include one or more of a heart rate sensor 488, a respiration sensor 490, a temperature sensor 492, and other sensors to obtain vital sign information. The heart rate sensor 488 and the respiration sensor 490 may be non-invasive sensors. The temperature sensor 492 may include temperature sensing transducers or fabrics. For example, thermistors may be provided in a piezoelectric sensing layer. The temperature sensors 492 may be configured to obtain one or both of the core body temperature and the skin temperature of the patient. Each of these physiological sensors 482 may be powered by the rechargeable battery 20.

Referring still to FIG. 24, the controller 36 may include routines 126 to monitor the information obtained by the physiological sensors 482. The controller 36 may also store previous information sensed by the physiological sensors 482 to compare subsequent information to determine a change in the physiological or vital sign information of the patient. The health monitoring system 480 may detect trends in the detected physiological parameters of the patient over time, which may be advantageous for detecting other health conditions. For example, certain changes in various physiological parameters may indicate sepsis. Additionally, after an initial assessment of the patient when admitted to the medical facility 12, a predetermined time may pass before a subsequent assessment is conducted, and the health monitoring system 480 may monitor the health of the patient between the initial assessment and any subsequent assessments.

The physiological information obtained by the physiological sensors 482 may be utilized to determine other diagnostic information, such as an apnea condition based on monitoring of a respiration rate from the force sensors 484 and the respiration sensors 490. A vibrating device, such as an apnea oscillator 494, within the mattress 48 or the patient support apparatus 14 may be activated by the controller 36 upon detection of an apnea condition to gently vibrate the patient and induce recovery. The apnea oscillator 494 is generally powered by the rechargeable battery 20. An alarm may be initiated via a vital sign alert 496 if the apnea condition persists beyond a predetermined period of time.

The controller 36 may also convey the information obtained by the physiological sensors 482 to the remote device 352, the user interface 144, or other systems. The controller 36 may also include routines 126 directed to monitoring the condition of the patient using the information obtained from the physiological sensors 482 and provide the vital sign alerts 496 when the vital signs of the patient are sensed to be outside a predetermined range. The predetermined range may be programmed by the caregiver and may be different for each vital sign.

The vital sign alerts 496 may be an informational alert, generally for minor deviations from the predetermined range, an emergency alert, generally for life-threatening deviations, or an intermediate alert. The vital sign alerts 496 may be communicated via the alert feature 34 or another alert system. The vital sign alerts 496 may also be communicated to the nurse call system 376. Additionally or alternatively, if the controller 36 detects a difference between initial physiological data and subsequent physiological data, the difference may be communicated to the caregiver. If the difference is at or above a predetermined threshold, the alarm may be communicated via the vital sign alert 496. The vital sign alert 496 may communicate via any wired or wireless communication and may be included in the alert feature 34.

Referring still to FIG. 24, the health monitoring system 480 may be utilized to determine if the patient is disposed on the patient support apparatus 14. When the force sensors 484 detect a weight on the patient support apparatus 14, the health monitoring system 480 confirms that a person is on the patient support apparatus 14. Additionally or alternatively, the health monitoring system 480 may be utilized to verify the identity of the patient on the patient support apparatus 14. For example, a sampling of vital signs data captured over a period of time and stored within the controller 36, the remote device 352, in the EMR, etc. may reveal a vitals sign "signature" of the patient. Sensed vital signs may be compared to the stored "signature" to verify the identity of the patient.

The health monitoring system 480 may also be in communication with the patient monitoring system 400 to determine optimized times to obtain physiological information from the patient. The patient monitoring system 400 may be utilized to determine the position of the patient on the patient support apparatus 14. Based on the sensed position of the patient, the controller 36 may activate the health monitoring system 480 to obtain the physiological data from the patient. For example, when the adjustable frame 200 is disposed with a head end elevated, which may be sensed by one of the sensors in any of the systems disclosed herein, the health monitoring system 480 may be activated. Additionally or alternatively, the controller 36 may operate to turn on the various physiological sensors 482 in response to a therapy protocol or as initiated by the caregiver.

The health monitoring system 480 may also be in communication with the pneumatic system 430. The controller 36 may adjust the amount of fluid within certain bladders 434 to provide an optimized pressure to the bladders 434. The physiological sensors 482, in combination with or independently of the patient monitoring system 400, may sense the position of the patient on the patient support apparatus 14, and the controller 36 may adjust the pneumatic system 430 in response. For example, if the patient adjusts onto his or her side, the controller 36 may adjust the pressure in bladders 434 to automatically minimize forces in different areas (e.g., torso, thigh, etc.) on the patient.

Referring still to FIG. 24, a microclimate management (MCM) system 498 may be selectively coupled with the patient support apparatus 14. When coupled with the patient support apparatus 14, the MCM system 498 is powered by the rechargeable battery 20. The MCM system 498 generally includes a blower 500, a top coverlet, and a spacer material within the top coverlet. The blower 500, powered by the rechargeable battery 20 and controlled by the controller 36, operates to direct or blow air through the spacer material. The MCM system 498 is generally disposed on a top surface of the mattress 48, and the patient may rest on the MCM system 498. While the patient is positioned on the MCM system 498, air is directed through the top coverlet. This configuration wicks away moisture from the skin of the patient by blowing air underneath the patient, which is advantageous for preventing skin conditions that may be caused by lying on the mattress 48 for an extended period of time. The MCM system 498 may be activated automatically when selectively coupled with the patient support apparatus 14, or may be activated through the user interface 144.

Referring still to FIG. 24, the patient support apparatus 14 may include a mattress comfort system 504 in fluid communication with the pneumatic system 430. The mattress comfort system 504 generally addresses shear, friction, pressure, and moisture properties of the mattress 48 in order to optimize patient comfort and keep the skin of the patient, cool and dry, which may aid in the prevention of complications and patient recovery, such as wound prevention. The mattress comfort system 504 may automatically make adjustments based on predetermined therapy functions or adjustments may be made manually based on user input commands received from the user interface 144. The pneumatic system 430 may provide air for the operation of the mattress comfort system 504. The mattress comfort system 504 may include various indicators, such as, for example, a floor indicator that projects an image from a projector 506 on the patient support apparatus 14, which may be powered by the rechargeable battery 20, to indicate information related to the mattress comfort system 504 and other features of the patient support apparatus 14 described herein.

Figure 25:
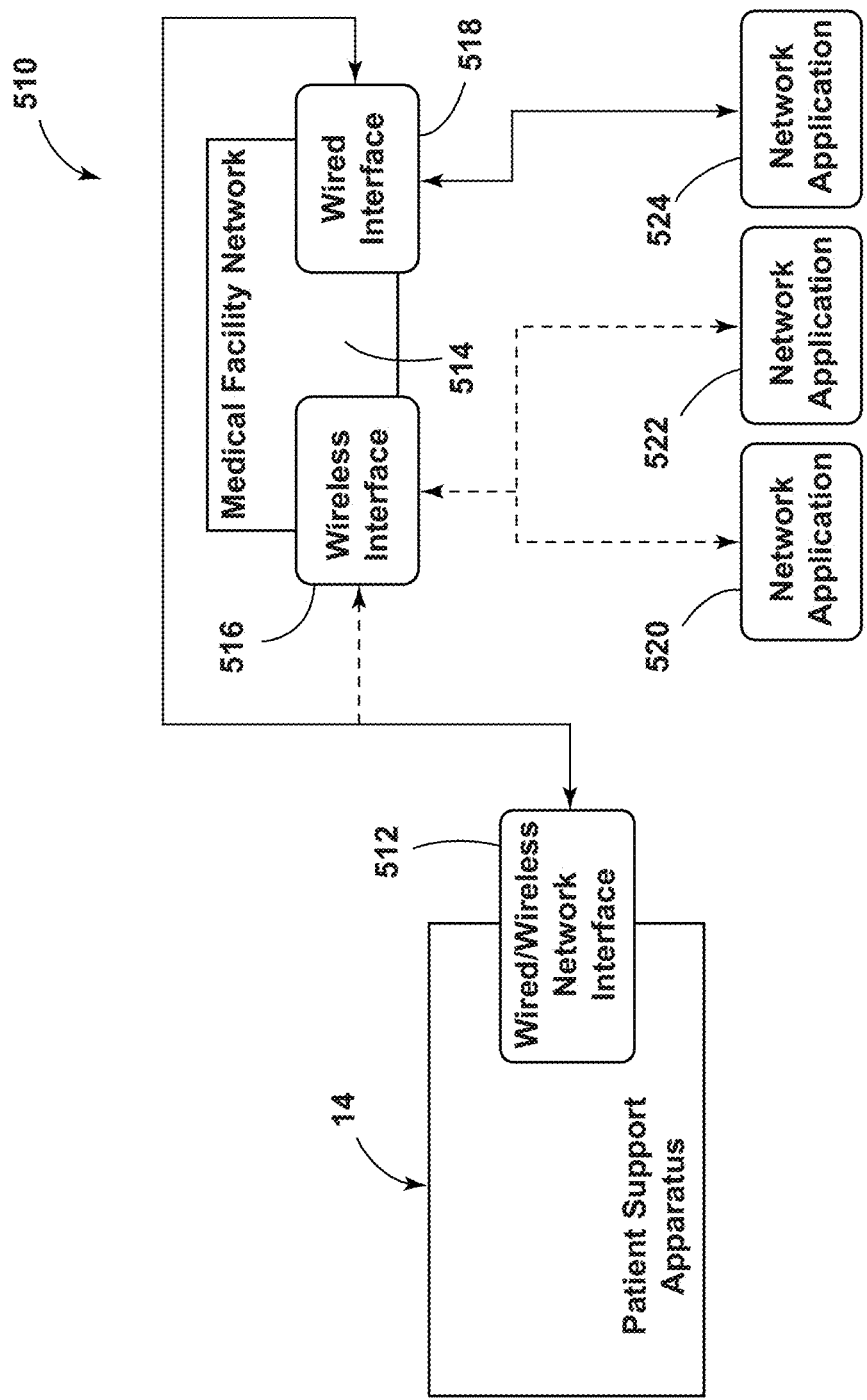
FIG. 25 is a block diagram of wired and wireless communications between a patient support apparatus and a medical facility, according to the present disclosure.

Referring now to FIG. 25, as previously discussed, the controller 36 communicates a variety of information to the remote device 352 and other systems or servers associated with the medical facility 12. Additionally or alternatively, the patient support apparatus 14 may include a communication system 510 for transmitting and receiving data and other information. In various examples, the communication system 510 includes a wired/wireless network interface 512 operably coupled with the patient support apparatus 14 for communicating with a medical facility network 514. The network interface 512 communicates with one or both of a wireless interface 516 and a wired interface 518 of the medical facility network 514. The data or information is then utilized by one or more network applications 520, 522, 524 in communication with the medical facility network 514. Exemplary network applications 520, 522, 524 include, for example, a nurse call software (e.g., of the nurse call system 376) that operates to contact assigned caregivers and other staff members of certain conditions of the patient or the patient support apparatus 14, a workflow software that assigns tasks to caregivers and other staff members, a locating-and-tracking software to track the location of people or equipment, an admission discharge and transfer software, a bed assignment software, etc.

Figure 26:
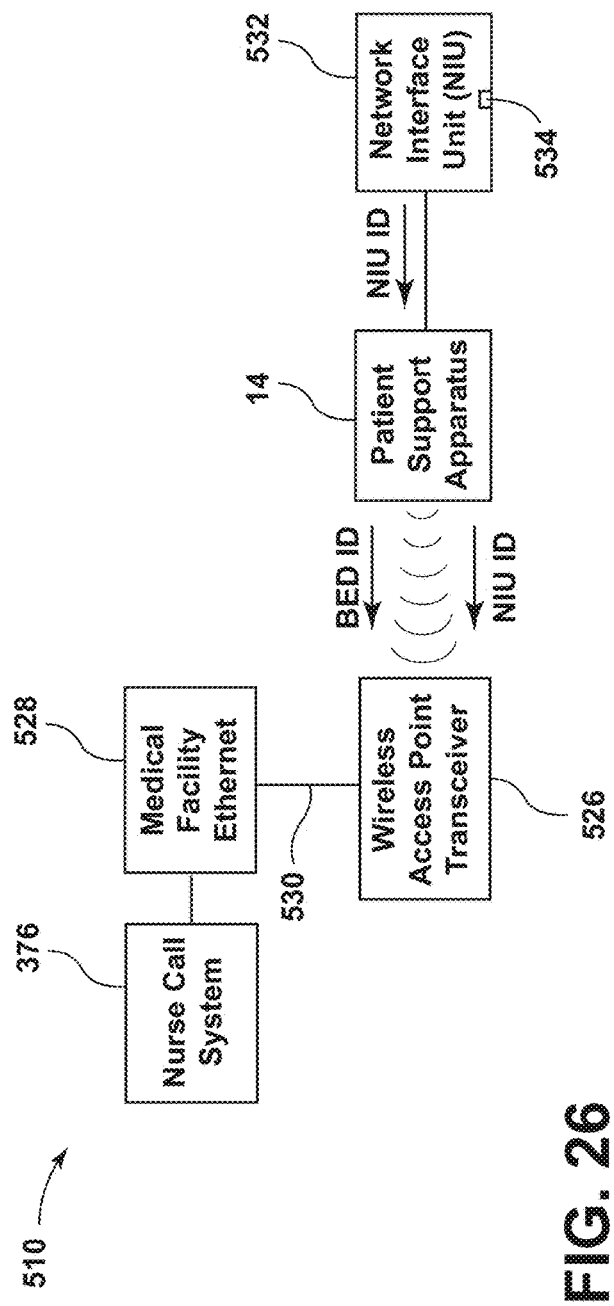
FIG. 26 is a block diagram of wireless communications between a patient support apparatus and a medical facility, according to the present disclosure.

Referring to FIG. 26, the patient support apparatus 14 may communicate with a wireless access point transceiver 526 that is coupled to Ethernet 528 of the medical facility 12. The communication system 510 of the patient support apparatus 14 provides for bidirectional communication between the patient support apparatus 14 and the wireless access point transceiver 526 according to a selected Ethernet protocol. The wireless access point transceiver 526 communicates bidirectionally with the Ethernet 528 via a data link 530.

Figure 27:
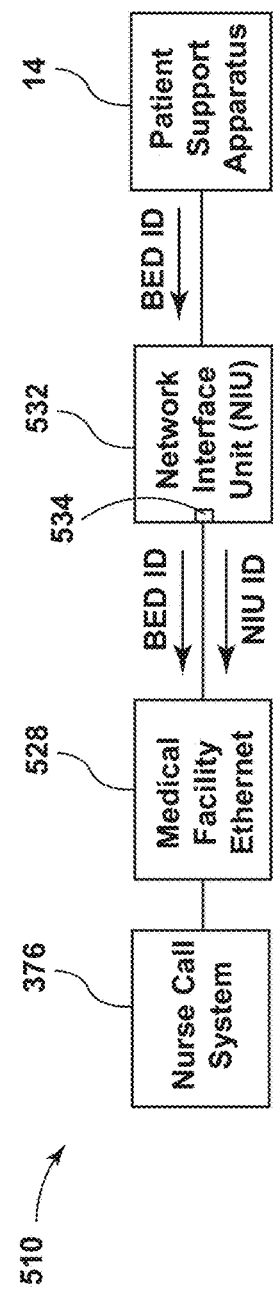
FIG. 27 is a block diagram of wired communications between a patient support apparatus and a medical facility, according to the present disclosure.

Referring to FIGS. 26 and 27, each patient support apparatus 14 may be associated with a network interface unit 532. Multiple network interface units 532 may be provided in various locations around the medical facility 12. It is contemplated that each patient support apparatus 14 may communicate with any one or more of the network interface units 532 within the medical facility 12. Each patient support apparatus 14 and each network interface unit 532 is assigned a unique identification (ID) code, such as a serial number. One or more of the devices of the nurse call system 376 or other remote devices 352 may have software that operates to associate bed ID data of the patient support apparatus 14 with network interface unit ID data of the network interface unit 532 to locate where each patient support apparatus 14 is positioned in medical facility 12.

Each network interface unit 532 includes a port 534 for selectively communicatively coupling with the Ethernet 528. If the network interface unit 532 is not directly coupled to the Ethernet 528 (e.g., via a wired connection), as illustrated in FIG. 26, the network interface unit 532 communicates the network interface unit ID to the patient support apparatus 14, which then wirelessly communicates the bed ID data and the network interface unit ID data to the wireless access point transceiver 526. Alternatively, if the network interface unit 532 is directly coupled to the Ethernet 528, as illustrated in FIG. 27, the associated patient support apparatus 14 communicates the bed ID to the network interface unit 532, which then communicates the bed ID and the network interface unit ID to the Ethernet 528 through wired communication.

Figure 28:
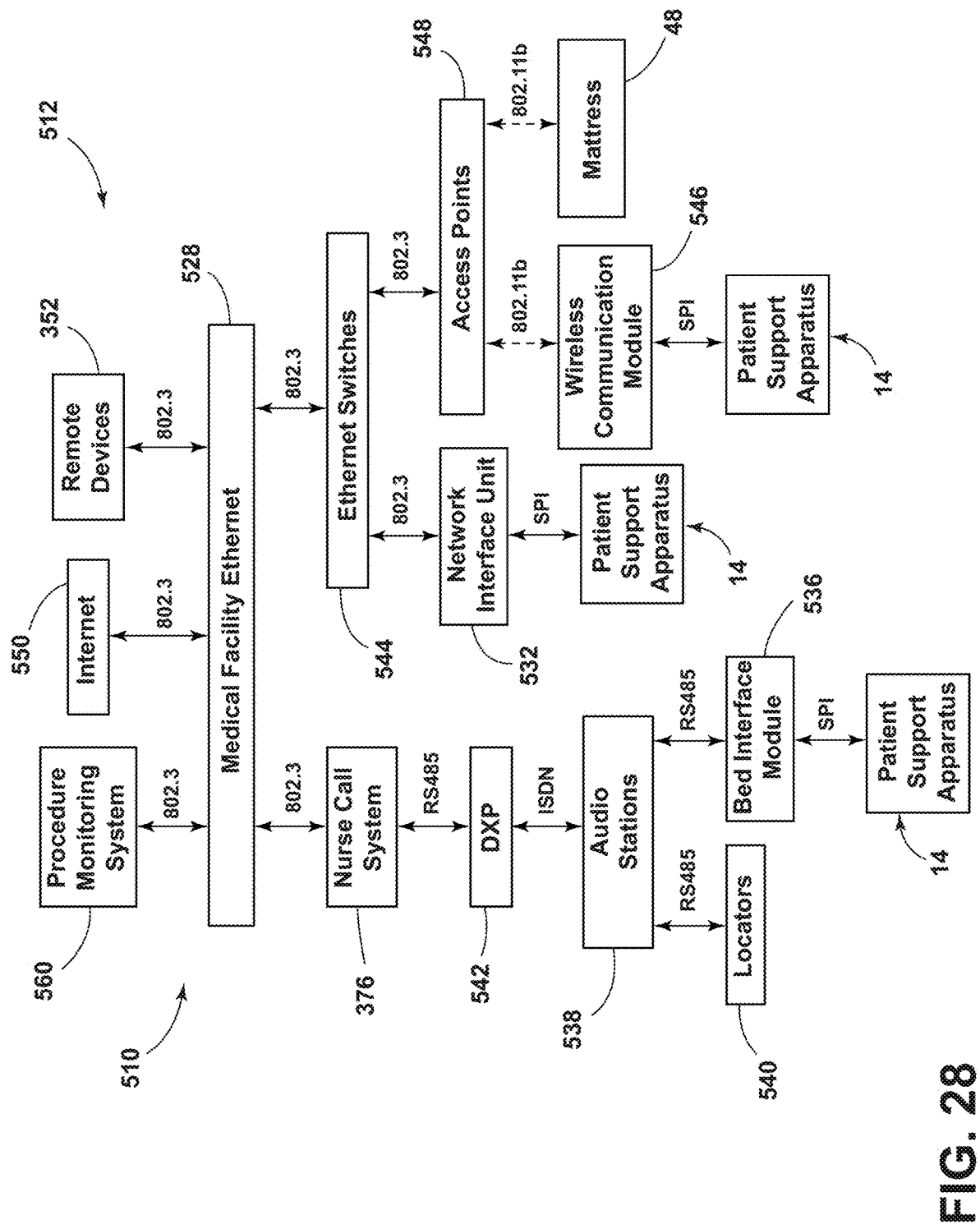
FIG. 28 is a block diagram of wireless data transfer between a patient support apparatus and a medical facility.

Referring to FIG. 28, the medical facility network 514 generally includes a plurality of patient support apparatuses 14 within the medical facility 12 that are each configured to communicate with other devices and systems of the medical facility network 514 through various communication paths. For example, each patient support apparatus 14 may be coupled to a bed interface module 536 via a wired serial interface (SPI) link, such as a 37-pin to a 37-pin cable. The bed interface module 536 may be coupled to audio stations 538 via a wired RS485 link.

Locators 540 (e.g., IR receivers or transceivers) of the locating-and-tracking system may be also coupled to the audio stations 538 via an RS485 link and are configured to receive wireless signals, such as IR signals, from locating-and-tracking badges utilized by the caregivers. The audio stations 538 are coupled to a Digital Phone Switch (DXP) 542. The DXP 542 is coupled to the nurse call system 376 via an RS485 link. The nurse call system 376 may display information received from the bed interface module 536, the audio stations 538, the DXP 542, or a combination thereof. The nurse call system 376 may be coupled to the Ethernet 528 via a wired link, such as an 802.3 protocol. The Ethernet 528, as illustrated in FIG. 28, is communicatively coupled with additional devices, medical equipment, and additional infrastructure (e.g. cables, outlets, connectors, routers, gateways, etc.) of the medical facility network 514.

The patient support apparatus 14 may be coupled to the network interface units 532 via a wired SPI link. The network interface units 532 are coupled to Ethernet switches 544 via 803.2 links, and the Ethernet switches 544 are coupled to the Ethernet 528 via 803.2 links. One or more remote devices 352 and other healthcare systems are coupled to the Ethernet 528. For example, one healthcare system may be a workflow software application. The workflow software application is operable to assign tasks to caregivers and other staff members of the facility 12.

Such workflow software may be, for example, NaviCare® software available from Hill-Rom Services, Inc. The workflow software application assigns tasks to staff members based on information received from patient support apparatus 14. In another example, the remote devices 352 or another healthcare system may have a nurse call software application. When the patient support apparatuses 14 are coupled to remote devices 352 through the network interface units 532 and the associated network infrastructure (e.g., the Ethernet switches 544, Ethernet 528, etc.), then the patient support apparatuses 14 transmit bed status data to the remote devices 352, alerting the caregiver to the status of the respective patient support apparatus 14 or the patient thereon.

Each patient support apparatus 14 is also capable of communicating wirelessly via a wireless communication module 546. The wireless communication modules 546 are substantially similar to the network interface units 532 described herein. The wireless communication modules 546 communicate via an SPI link with circuitry 350 of the associated patient support apparatus 14 and communicate via a wireless 802.11b link with wireless access points 548 that are located throughout the medical facility 12. The wireless access points 548 are coupled to the Ethernet switches 544 via 802.3 links. It is contemplated that the wireless communication modules 546 may communicate with the wireless access points 548 according to any wireless protocol, such as 802.11g protocol, Bluetooth® protocol, ZigBee® protocol, etc. The Ethernet 528 may also be coupled to Internet 550 via an 802.3 link.

When the patient support apparatus 14 is coupled to the remote devices 352 through the wireless communication modules 546 and the associated network infrastructure, the patient support apparatuses 14 wirelessly transmit bed status data. It is contemplated that each patient support apparatus 14 disclosed herein has a variety of connectivity options. Further, each remote device 352 and remote system, including the nurse call system 376, is configured to send data to other remote devices 352 coupled to the Ethernet 528 or the Internet 550 to form a communication network within the medical facility 12.

Referring still to FIG. 28, data from the patient support apparatus 14 may be routed to different remote devices 352 or to different software programs within the same remote device 352. Information and data that may be communicated between the patient support apparatus 14 and the medical facility network 514 includes, but is not limited to, bed position data, brake status data, fall prevention protocol status, upper frame position data, rail position data, surface prevent mode data (e.g., for prevention of pressure ulcers), bed exit system data, patient movement data, lift system status, adjustable frame status, turn assist mode, max inflate mode of the pneumatic system 430, rotation mode status, percussion or vibration mode status, MCM system data, housekeeping information, rechargeable battery 20 status, nurse call data, bed information (e.g., manufacturer, model number, etc.), bed location information, patient physiological information, etc.

Each type of information may include a destination address, such as an Internet Protocol (IP) address, of the remote device 352 for which the particular information or data is destined. Additionally or alternatively, different information or data may be routed to different software applications based on the type of information or data being transmitted. The transmitted information or data may also include the bed ID or other identification information of the patient support apparatus 14 from which the information was transmitted. Further, the information or data may include location data, such as a room number or other location ID indicating the location of the associated patient support apparatus 14. The IP address of each patient support apparatus 14 may be assigned by one or more remote devices 352 communicatively coupled to the Ethernet 528.

It is contemplated that the mattress 48 may be associated with wireless communication modules 546 to communicate a variety of information relating to the mattress 48. The mattress 48 and the patient support apparatus 14 may communicate with one or more of the same wireless access points 548. Generally, such wireless communication may be at different frequencies and/or at different times. Thus, the wireless communication circuitry 350 of patient support apparatus 14 and the wireless communication circuitry of mattress 48 operate independently of each other. It is also contemplated that the controller 36 may communicate with the medical facility network 514 via any wired or wireless communication protocol without departing from the teachings herein.

Referring still to FIG. 28, a procedure monitoring system 560 may be in communication with the patient support apparatus 14, which confirms that various internal procedures are followed by the caregiver. The internal procedures may be programmed into the controller 36 and stored in the memory 124, or alternatively communicated to the controller 36 through wired or wireless communication protocols. For example, if a fall risk protocol is initiated, the procedure monitoring system 560 may monitor whether the caregiver is alerted when the patient monitoring system 400 indicates the patient is attempting to exit the patient support apparatus 14.

In another non-limiting example, if a pulmonary risk protocol is activated, the procedure monitoring system 560 may monitor whether a head portion of the patient is maintained in an elevated position. The controller 36 may store data received from various systems described herein and the data may be compared to activated protocols for a specific patient or the specific patient support apparatus 14. The compared information may be communicated via the controller 36 or the communication system 510 to various remote devices 352 within the medical facility 12 where the caregiver can review the comparison. The detected information compared to the activated protocols can confirm whether proper procedures were followed or whether there was a deviation. The information regarding deviations or compliance may be reviewed by the caregiver and may be stored in the EMR for the patient. Any aspects of the procedure monitoring system 560 incorporated into or coupled to the patient support apparatus 14 may be powered by the rechargeable battery 20.

Referring to FIGS. 1-28, the patient support apparatus 14 may be moved freely about the medical facility 12. The use of the charging system 10 and the rechargeable battery 20 reduces or eliminates cords that are associated with the patient support apparatus 14. Cordless patient support apparatuses 14 have a variety of advantages, including more convenient movement between different locations within the room environment 356 or the medical facility 12 in general. Additionally or alternatively, the cordless patient support apparatus 14 may be advantageous for patients determined to have behavioral health risks or concerns. Cords, including power cords on other patient supports, may be a harm risk for those patients who have behavioral health risks or concerns. The removal of the cord as provided by the rechargeable battery 20 and the charging system 10 of the present disclosure, reduces the harm risk for these patients. Accordingly, the cordless patient support apparatus 14 disclosed herein may provide safety benefits for use with patients having behavioral health risks or concerns.

The rechargeable battery 20 is charged by the charging system 10 in various locations around the medical facility 12 and powers the various powered components 100 of the patient support apparatus 14 described herein. The various powered components 100 described herein are exemplary and are not meant to be limiting. The patient support apparatus 14 may include any one or more of the various powered components 100 described herein. The flexibility of the charging system 10 to charge the rechargeable battery 20 provides more convenience for powering the various components 100 of the patient support apparatus 14 as the patient support apparatus 14 is moved to different locations within the medical facility 12.

Moreover, providing power to the components 100 allows greater flexibility for treating the patient and reduces worry of the caregiver about loss of power during treatment and therapies. Time the caregiver has for treating the patient may be increased when the caregiver does not have to repeatedly plug and unplug a support apparatus into the power source 86. This may be advantageous if the caregiver quickly moves the patient support apparatus 14 in response to a condition of the patient (e.g., to another unit, to testing, etc.). The caregiver is also alerted when the rechargeable battery 20 is below the predetermined power threshold, providing time for the caregiver to align the receiving assembly 30 with the transmitting assembly 22 prior to the rechargeable battery 20 reaching the empty charge level. The rechargeable battery 20 provides increased flexibility for the patient support apparatus 14, the components 100, and the caregiver.

Further, the medical facility 12 may have a variety of power sources 86, such as, but not limited to, a 120V power source, a 240V power source, a 480V power source, etc. The charging system 10 may be configured to be associated with more than one or all of the power sources 86. For example, in certain locations of the medical facility 12, the more commonly available power source 86 may be the 120V power source. The transmitting assembly 22 may be configured to be in electrical communication with the 120V power source. In other locations of the medical facility 12, the more commonly available power source may be the 240V power source. In such circumstances, the transmitting assembly 22 may be configured to be in electrical communication with the 240V power source. Accordingly, the transmitting assembly 22 may be configured to be in electrical communication with the 120V power source, the 240V power source, or any other power source 86 interchangeably. This configuration allows more flexibility for charging the rechargeable battery 20 in a variety of different locations within the medical facility 12, which may have different types of power sources 86 available.

Use of the present device may provide for a variety of advantages. For example, the wireless charging from the charging system 10 may provide efficient and convenient charging of the rechargeable battery 20. Additionally, the rechargeable battery 20 may be partially charged throughout the day in various locations in the medical facility 12. Further, the rechargeable battery 20 may have a high capacity to hold a charge, which may result in a single charge powering the patient support apparatus 14 for at least 12 hours.

Further, the transmitting assemblies 22 may be arranged in various locations in the medical facility 12 and may be disposed on or proximate to one or both of the wall surface 26 and the floor surface 28. Additionally, the receiving assembly 30 receives energy from the transmitting assembly 22, which may be operably coupled to the wall surface 26, the floor surface 28, or a combination thereof. The receiving assembly 30 that includes the floor secondary element 74 and the wall secondary element 76 may increase flexibility in the charging location of the patient support apparatus 14 provided through the floor and wall secondary elements 74, 76, respectively. Also, the user interface 144 and/or the alert feature 34 may provide one or more alerts to the medical personnel of the current charge level of the rechargeable battery 20 to minimize loss of power to the patient support apparatus 14. Moreover, proper alignment of the receiving assembly 30 relative to the transmitting assembly 22 may be confirmed through the alignment feature 140. Further, the charge disruption feature 170 may alert the caregiver that the rechargeable battery 20 is no longer charging.

Additional advantages may include the ability to power one or more of the powered components 100 with the rechargeable battery 20. Further, the wireless charging system 10 creates greater flexibility with the powered components 100 included on the patient support apparatus 14 that are supported by the rechargeable battery 20. Additionally, the charging system 10 reduces the time for the caregiver to ready the patient support apparatus 14 for a patient. The caregiver may not spend time finding an outlet and plugging the patient support apparatus 14 into the outlet with the wireless charging system 10.

Further, the wireless charging system 10 is utilized to charge the powered components 100, reducing time the caregiver spends on determining whether the powered components 100 are charged or searching for separate outlets for the powered components 100. Also, the wireless charging system 10 reduces cords around the patient support apparatus 14. The reduction in cords may reduce tripping hazards for the caregiver and other medical personnel. Additionally, the reduction in cords may reduce electrocution hazards.

Further, the reduction in cords may reduce safety hazards for those under behavioral health monitoring. Moreover, the reduction in cords removes potential obstacles for movement of the patient support apparatus 14 or other equipment within the room environment 356 and elsewhere in the medical facility 12. Additional advantages and benefits of using this device may be realized and/or achieved.

The device disclosed herein is further summarized in the following paragraphs and is further characterized by combinations of any and all of the various aspects described therein.

According to one aspect of the present disclosure, a charging system for a medical facility includes a patient support apparatus that has a base frame, an upper frame coupled to the base frame, a wheel operably coupled to the base frame to engage a floor surface, and a controller operably coupled to at least one of the base frame and the upper frame. A rechargeable battery is operably coupled to the base frame. The controller is configured to communicate with the rechargeable battery. A transmitting assembly is coupled to at least one of a wall surface and the floor surface of said medical facility. A receiving assembly is operably coupled to the base frame adjacent to the wheel. The receiving assembly is in communication with the rechargeable battery. The receiving assembly and the transmitting assembly selectively communicate to charge the rechargeable battery. An alert feature is in communication with the controller of the patient support apparatus. The alert feature is configured to emit an alarm when the controller indicates the rechargeable battery is at or below a predetermined charge level.

According to another aspect, a receiving assembly and a transmitting assembly are configured to communicate via capacitive coupling to charge a rechargeable battery.

According to another aspect, a user interface in communication with a controller. The user interface includes a display that has an icon indicating a current charge level of a rechargeable battery.

According to another aspect, an alert feature includes at least one of a speaker to emit an audible alarm and a light source to emit a visual alarm.

According to another aspect, an indicator light is operably coupled to at least one of a patient support apparatus, a rechargeable battery, and a transmitting assembly. The indicator light illuminates when the rechargeable battery is in a charging state.

According to another aspect, a sensor is operably coupled to a receiving assembly. The sensor is configured to sense at least one of an electric field and an electromagnetic field emitted by a transmitting assembly to initiate charging of a rechargeable battery.

According to another aspect, a transmitting assembly is operably coupled to a wall surface. A receiving assembly is configured to be oriented toward the wall surface.

According to another aspect, a transmitting assembly is operably coupled to a floor surface. A receiving assembly is configured to be oriented toward the floor surface.

According to another aspect, a power drive system is operably coupled to a base frame of a patient support apparatus. The drive system includes a drive wheel operably coupled with a motor via a clutch. The motor is operably coupled to the rechargeable battery.

According to another aspect of the present disclosure, an apparatus charging system includes a patient support apparatus including a base frame, wheels coupled to the base frame and configured to engage a floor surface, and a controller. A rechargeable battery is coupled to the patient support apparatus and in communication with the controller. A receiving assembly is coupled to the patient support apparatus. The receiving assembly is coupled to the base frame at a height that is approximately equal to a height of the wheel. The receiving assembly is in communication with the rechargeable battery. A transmitting assembly is configured to selectively communicate with the receiving assembly to charge the rechargeable battery.

According to another aspect, a lift system is operably coupled to a base frame and an upper frame for adjusting the upper frame relative to the base frame. The lift system includes an actuator that is operably coupled to the rechargeable battery.

According to another aspect, a receiving assembly includes a floor secondary element oriented in a first direction toward a floor surface and a wall secondary element oriented in a second direction toward a wall surface. A transmitting assembly includes a floor primary element operably coupled to the floor surface and a wall primary element operably coupled to the wall surface.

According to another aspect, a pneumatic system is disposed within a mattress selectively positioned on an upper frame of a patient support apparatus. The pneumatic system includes a pump operably coupled with a rechargeable battery. The pump is in fluid communication with bladders to selectively adjust the bladders between an inflated condition and a deflated condition.

According to another aspect, a health monitoring system is operably coupled with a patient support apparatus and a rechargeable battery. The health monitoring system includes at least one physiological sensor for sensing a physiological parameter of a patient disposed on the patient support apparatus.

According to another aspect, a communication system is coupled to a patient support apparatus. The communication system includes a wireless communication module operably coupled with a rechargeable battery.

According to another aspect, a powered component is coupled to a patient support apparatus and operably coupled to a rechargeable battery. The powered component includes at least one of a brake system, an adjustable frame having an actuator, a patient monitoring system to sense patient movement, an obstacle detection system, a microclimate management system, and a mattress comfort system.

According to another aspect of the present disclosure, a charging system for a medical facility includes a patient support apparatus that has a frame. A wheel is operably coupled to the frame to engage a floor surface. A transmitting assembly has a floor primary element operably coupled to the floor surface and a wall primary element operably coupled to a wall surface in the medical facility. A rechargeable battery is operably coupled to the patient support apparatus. A receiving assembly has a floor secondary element oriented in a first direction to communicate with the floor primary element and a wall secondary element oriented in a second direction to communicate with the wall primary element. The transmitting assembly and the receiving assembly selectively communicate to charge the rechargeable battery.

According to another aspect, an alignment feature is in communication with a controller of a patient support apparatus. The alignment feature confirms proper positioning of the receiving assembly relative to the transmitting assembly.

According to another aspect, a charge disruption feature is in communication with a controller. The charge disruption feature indicates that charging of a rechargeable battery has been disrupted prior to the rechargeable battery reaching a predetermined charge level.

According to another aspect, a powered component is coupled to a patient support apparatus and operably coupled to a rechargeable battery. The powered component includes at least one of a power drive system, a brake system, a lift system, an adjustable frame having an actuator, a patient monitoring system, an obstacle detection system, a pneumatic system, a health monitoring system, a microclimate management system, a mattress comfort system, and a communication system.

According to another aspect, a means for charging in a medical facility includes a means for supporting a patient that has a base frame and an upper frame. A means for providing power is operably coupled to the base frame. A means for transmitting includes a primary element. The means for transmitting is operably coupled to at least one of a wall surface and a floor surface. A means for receiving is operably coupled to the base frame. The means for receiving includes a secondary element. The primary element and the secondary element selectively communicate via at least one of capacitive coupling and inductive coupling. A means for alerting is operably coupled to the patient support apparatus. The means for alerting activates an alarm when the means for providing power is at or below a predetermined charge level.

Related applications, for example those listed herein, are fully incorporated by reference. Descriptions within the related applications are intended to contribute to the description of the information disclosed herein as may be relied upon by a person of ordinary skill in the art. Any changes between any of the related applications and the present disclosure are not intended to limit the description of the information disclosed herein, including the claims. Accordingly, the present application includes the description of the information disclosed herein as well as the description of the information in any or all of the related applications.

It will be understood by one having ordinary skill in the art that construction of the described disclosure and other components is not limited to any specific material. Other exemplary embodiments of the disclosure disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

What is claimed is:

1. A charging system for a medical facility, comprising: a patient support apparatus including: a base frame having a head end; an upper frame coupled to the base frame; a wheel operably coupled to the base frame to engage a floor surface, and a controller operably coupled to at least one of the base frame and the upper frame; a rechargeable battery operably coupled to the base frame, wherein the controller is configured to communicate with the rechargeable battery; a transmitting assembly including a wall primary element configured to be coupled to a wall surface and a floor primary element configured to be coupled to the floor surface of said medical facility, wherein the wall primary element is configured to be positioned above the wheel and spaced from the floor surface by a distance equal to a height of the wheel;
   a receiving assembly coupled to the base frame at the head end adjacent to the wheel, wherein the receiving assembly is in communication with the rechargeable battery, and wherein the receiving assembly includes a wall secondary element and a floor secondary element spaced from the floor surface at a distance equal to the height of the wheel and oriented in different directions to selectively communicate with the floor primary element and the wall primary element, respectively, to charge the rechargeable battery, and further wherein the wall secondary element is oriented and fixed in a first direction outward from the head end away from a foot end of the base frame and the floor secondary element is oriented and fixed in a second direction toward the floor surface; and an alert feature in communication with the controller of the patient support apparatus, wherein the alert feature is configured to emit an alarm when the controller indicates the rechargeable battery is at or below a predetermined charge level.

2. The charging system of claim 1, wherein the receiving assembly and the transmitting assembly are configured to communicate via capacitive coupling to charge the rechargeable battery.

3. The charging system of claim 1, further comprising:
   a user interface in communication with the controller, wherein the user interface includes a display having an icon indicating a current charge level of the rechargeable battery.

4. The charging system of claim 1, wherein the alert feature includes at least one of a speaker to emit an audible alarm and a light source to emit a visual alarm.

5. The charging system of claim 1, further comprising:
an indicator light operably coupled to at least one of the patient support apparatus, the rechargeable battery, and the transmitting assembly, wherein the indicator light illuminates when the rechargeable battery is in a charging state.

6. The charging system of claim 1, further comprising:
a sensor operably coupled to the receiving assembly, wherein the sensor is configured to sense at least one of an electric field and an electromagnetic field emitted by the transmitting assembly to initiate a charging of the rechargeable battery.

7. The charging system of claim 1, further comprising:
a power drive system operably coupled to the base frame of the patient support apparatus, wherein the power drive system includes a drive wheel operably coupled with a motor via a clutch, wherein the motor is operably coupled to the rechargeable battery.

8. The charging system of claim 1, wherein the first direction is perpendicular to the second direction.

9. The charging system of claim 1, wherein the floor primary element and the wall primary element are each disposed within a protective housing, respectively.

10. The charging system of claim 1, wherein the receiving assembly includes a protective housing feature, and wherein the wall and floor secondary elements are disposed within the protective housing feature.

11. The charging system of claim 1, wherein the upper frame is movable relative to the base frame, and wherein the receiving assembly is configured to selectively communicate with the wall primary element when the upper frame is disposed at multiple heights and angles relative to the base frame.

12. The charging system of claim 1, further comprising:
a sensor operably coupled to the transmitting assembly, wherein the sensor is configured to sense at least one of an electric field and an electromagnetic field emitted by the transmitting assembly to initiate a charging of the rechargeable battery.

13. The charging system of claim 1, further comprising:
an object sensor operably coupled to the base frame, wherein the object sensor is configured to sense objects disposed between the transmitting assembly and the receiving assembly.

14. The charging system of claim 1, wherein the receiving assembly is positioned between five inches and twelve inches from the transmitting assembly to communicate and charge the rechargeable battery.

\* \* \* \* \*